US010973900B2

(12) United States Patent
Jully et al.

(10) Patent No.: US 10,973,900 B2
(45) Date of Patent: Apr. 13, 2021

(54) DRIED COMPOSITION

(71) Applicant: GlaxoSmithKline Biologicals SA, Rixensart (BE)

(72) Inventors: Vanessa Jully, Rixensart (BE); Erwan Bourles, Rixensart (BE)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 0 days.

(21) Appl. No.: 16/613,111

(22) PCT Filed: May 11, 2018

(86) PCT No.: PCT/EP2018/062233
§ 371 (c)(1),
(2) Date: Nov. 12, 2019

(87) PCT Pub. No.: WO2018/206776
PCT Pub. Date: Nov. 15, 2018

(65) Prior Publication Data
US 2020/0188499 A1    Jun. 18, 2020

(30) Foreign Application Priority Data
May 12, 2017  (GB) ..................................... 1707700

(51) Int. Cl.
*A61K 39/04*    (2006.01)
*A61K 9/19*     (2006.01)
*A61K 39/00*    (2006.01)

(52) U.S. Cl.
CPC ................ *A61K 39/04* (2013.01); *A61K 9/19* (2013.01); *A61K 2039/55555* (2013.01); *A61K 2039/55577* (2013.01)

(58) Field of Classification Search
None
See application file for complete search history.

(56) References Cited

U.S. PATENT DOCUMENTS 9,675,554 B1    6/2017  Gregoriadis et al.
2014/0234403 A1 8/2014  De Kesel et al.

FOREIGN PATENT DOCUMENTS

| WO | 9633739 A1 | 10/1996 | |
| WO | 2010142686 A1 | 12/2010 | |
| WO | WO 2012/080369 A1 | 6/2012 | |
| WO | WO-2012080369 A1 * | 6/2012 | ............. A61P 37/04 |
| WO | 2017102737 A1 | 6/2017 | |

OTHER PUBLICATIONS

Christensen et al (Biochim. Biophysic. Acta, 1768:2120-2129, 2007).*
Leroux-Roels et al., Vaccine, 31:2196-2206 (2013).
Montoya et al., Journal of Clinical Immunology, 33:1360-1375 (2013).
Thacher et al., AIDS, 28:1769-1781 (2014).
Idoko et al., Tuberculosis, 94:564-578 (2014).
Ingvarsson et al., J Controlled Release, 167:256-264 (2013).
Mohammed et al., Methods, 40:30-38 (2006).
Orr et al., J. Controlled Release, 177:20-26 (2014).
Penn-Nicholson et al., Vaccine, 33:4025-4034 (2015).
International Search Report and Written Opinion in corresponding International Application No. PCT/EP2018/062233, dated Oct. 5, 2018 (10 pages).

* cited by examiner

*Primary Examiner* — Brian Gangle

(57) ABSTRACT

A composition dried under reduced pressure from a liquid mixture comprising: an adjuvant which comprises a TLR-4 agonist and a saponin in a liposomal formulation, wherein the liposomes contain a neutral lipid and a sterol, amorphous sugar, wherein the amorphous sugar is present in an amount of more than 7.5% (w/v) of the liquid mixture, and an antigen derived from *Mycobacterium tuberculosis*.

25 Claims, 14 Drawing Sheets
Specification includes a Sequence Listing.

Figure 1-A
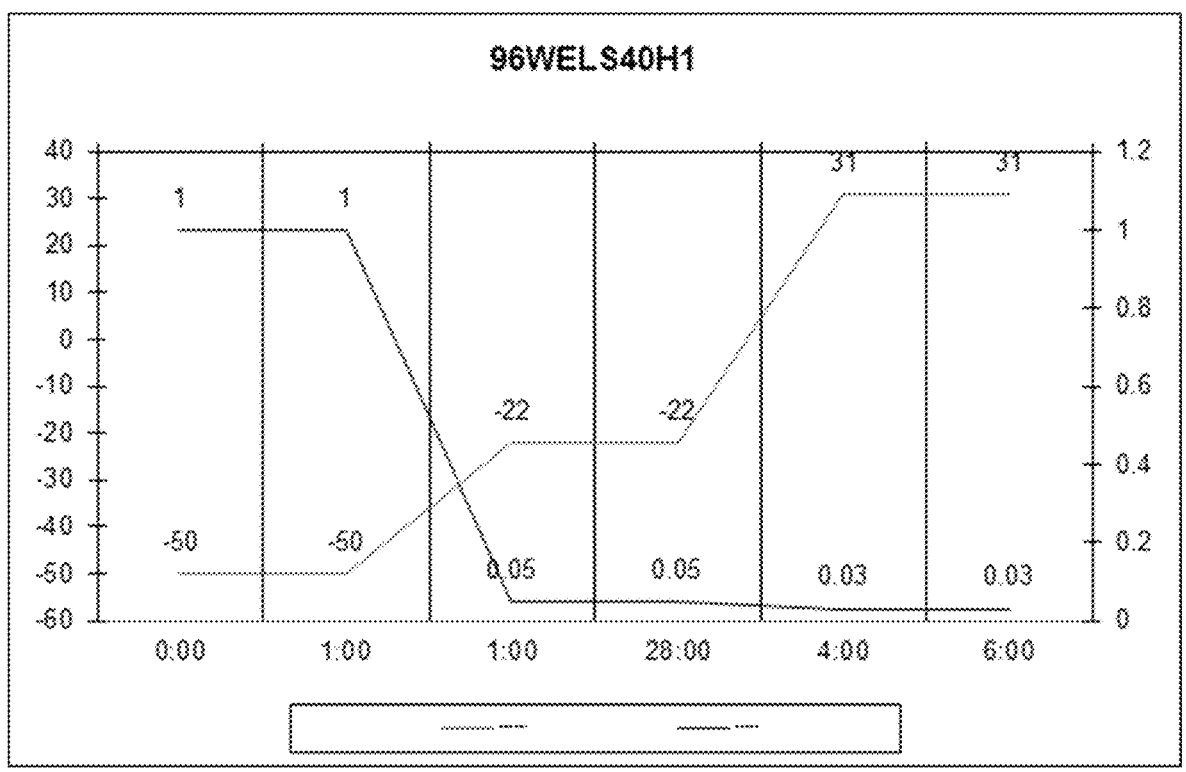

Figure 1-B
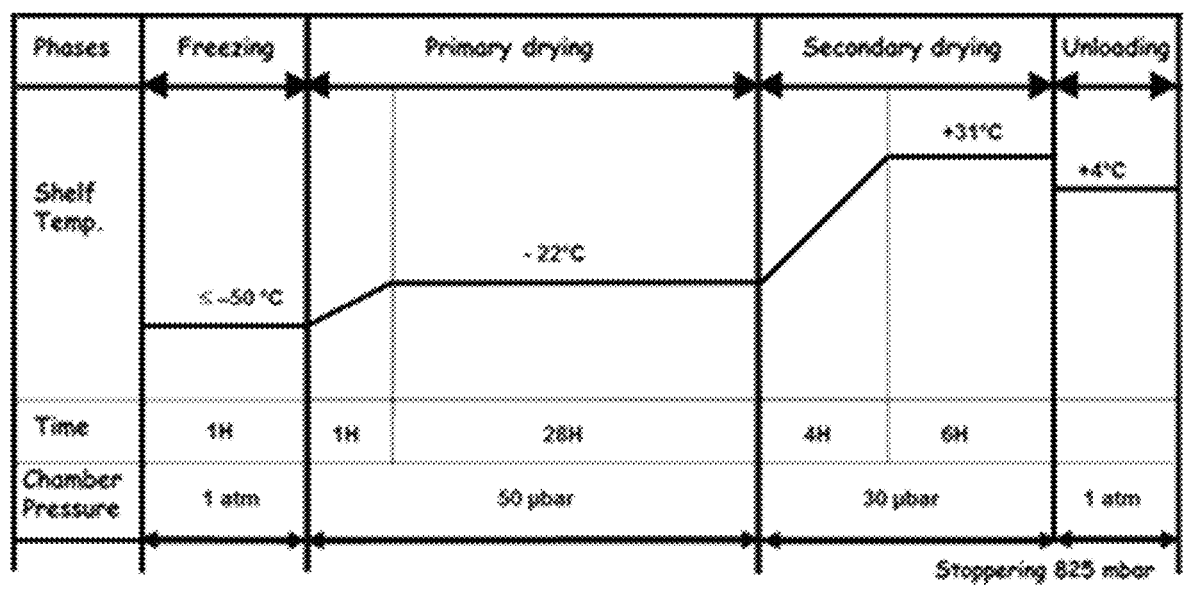

Figure 2-A
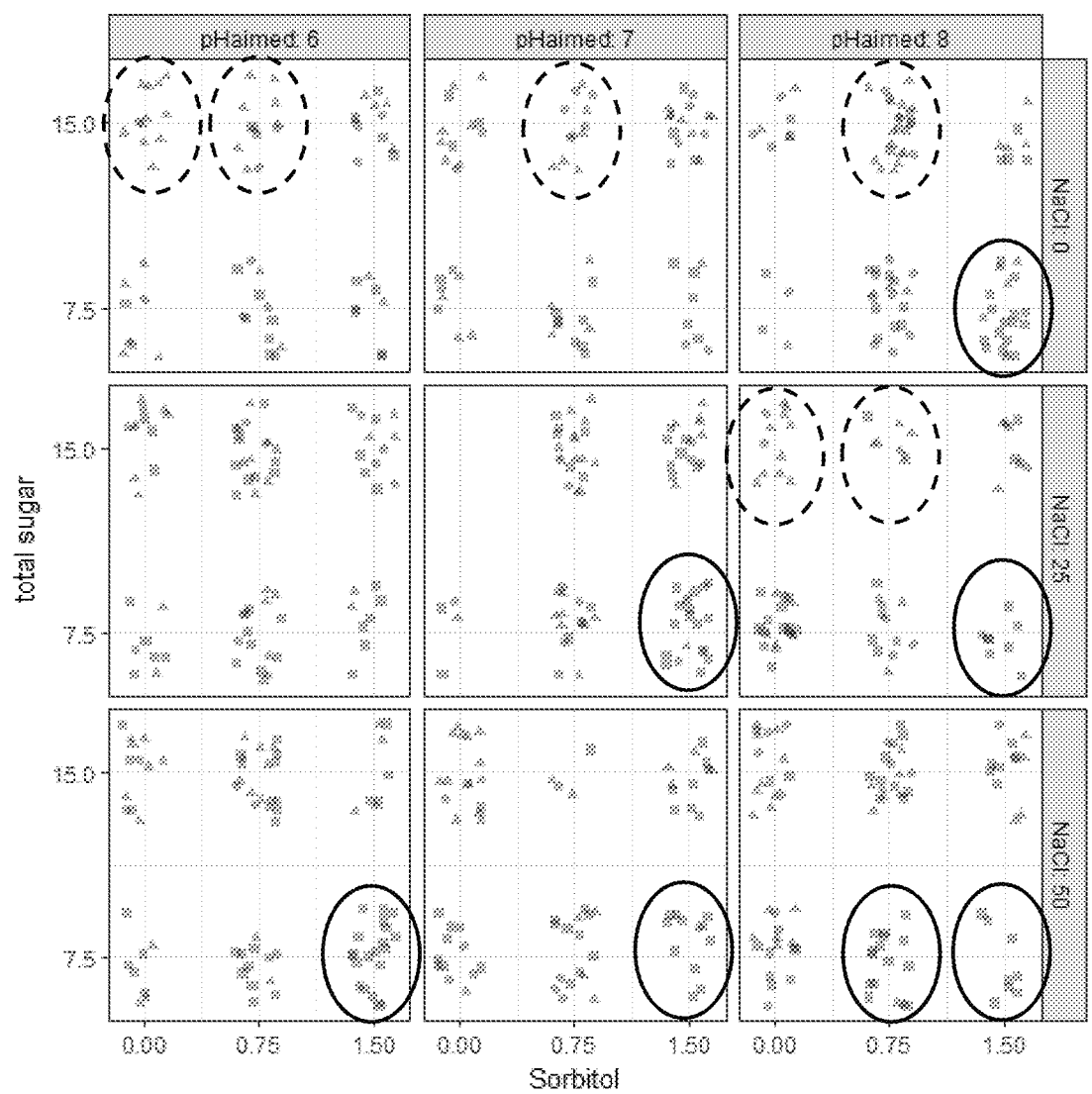

Figure 2-B
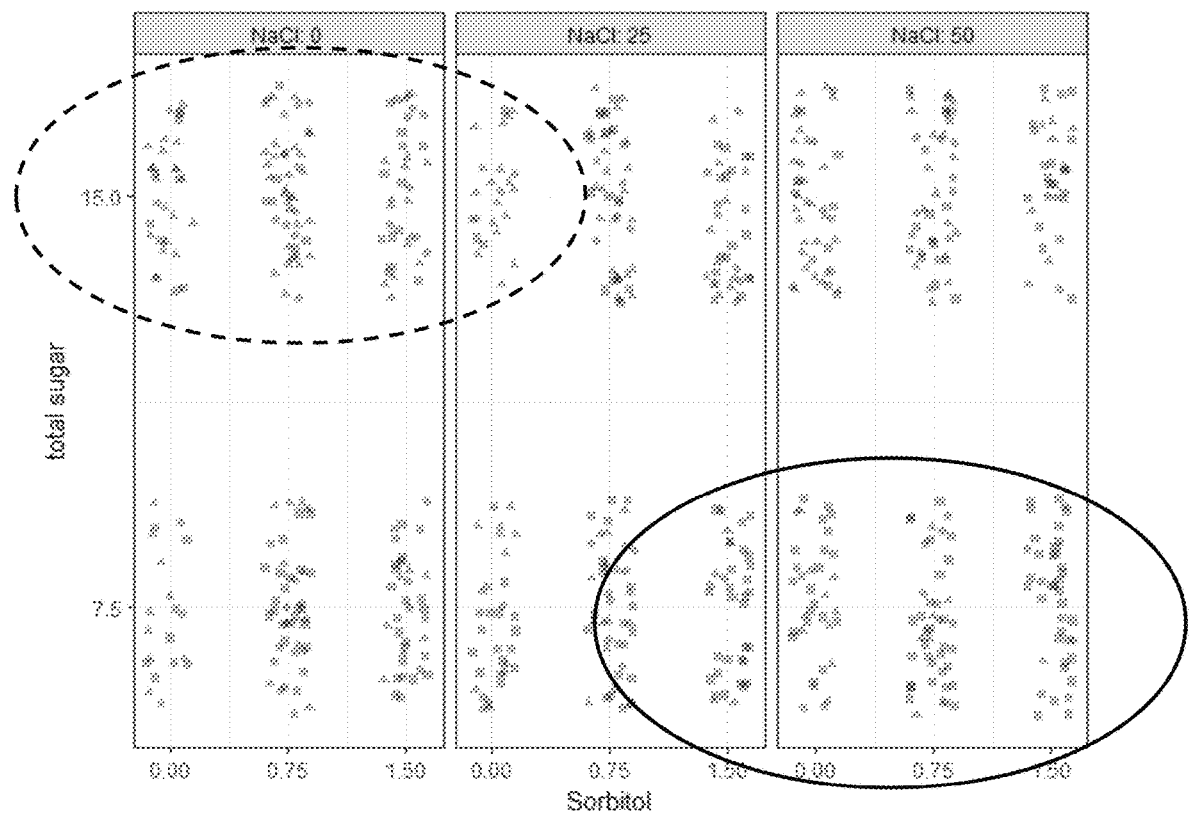

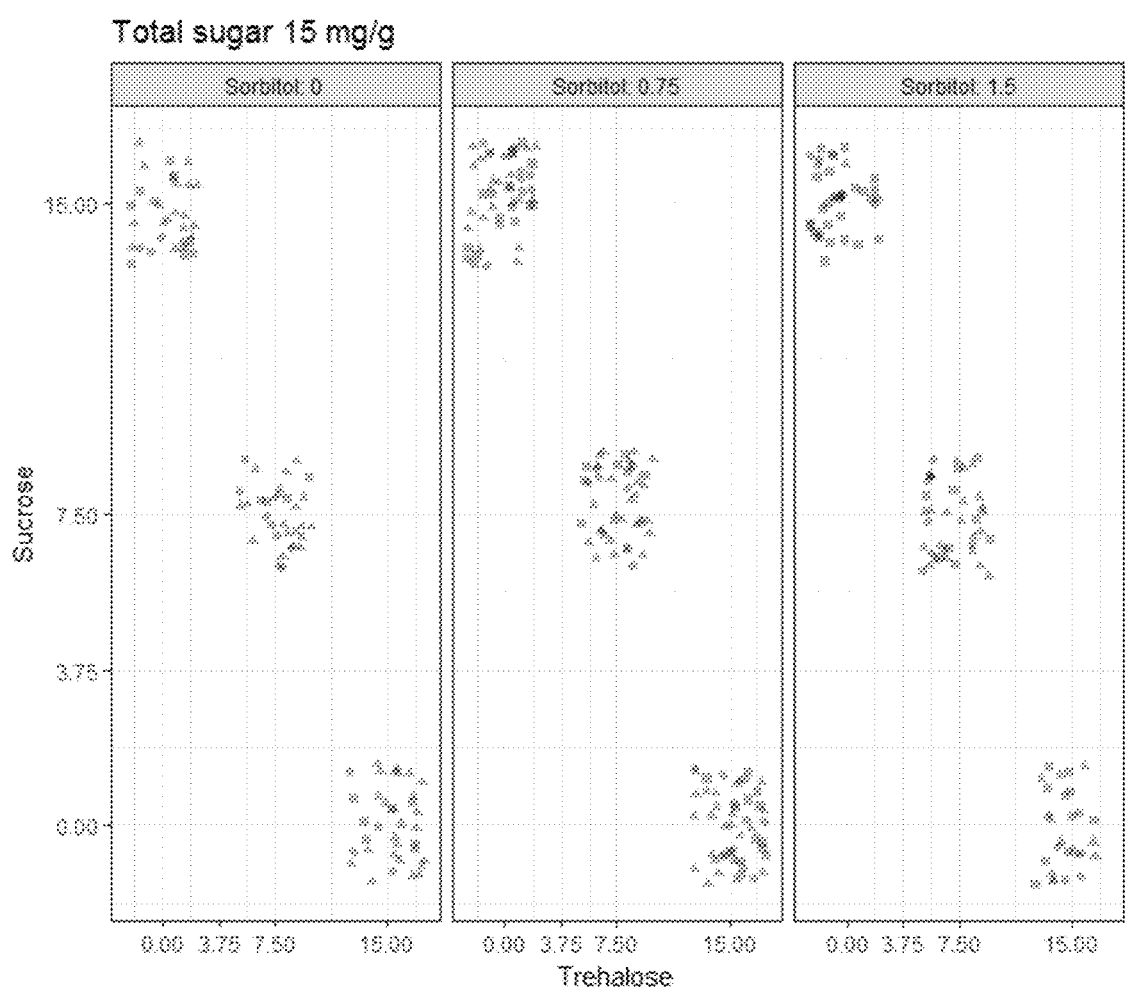
Figure 2-C

Figure 4-A
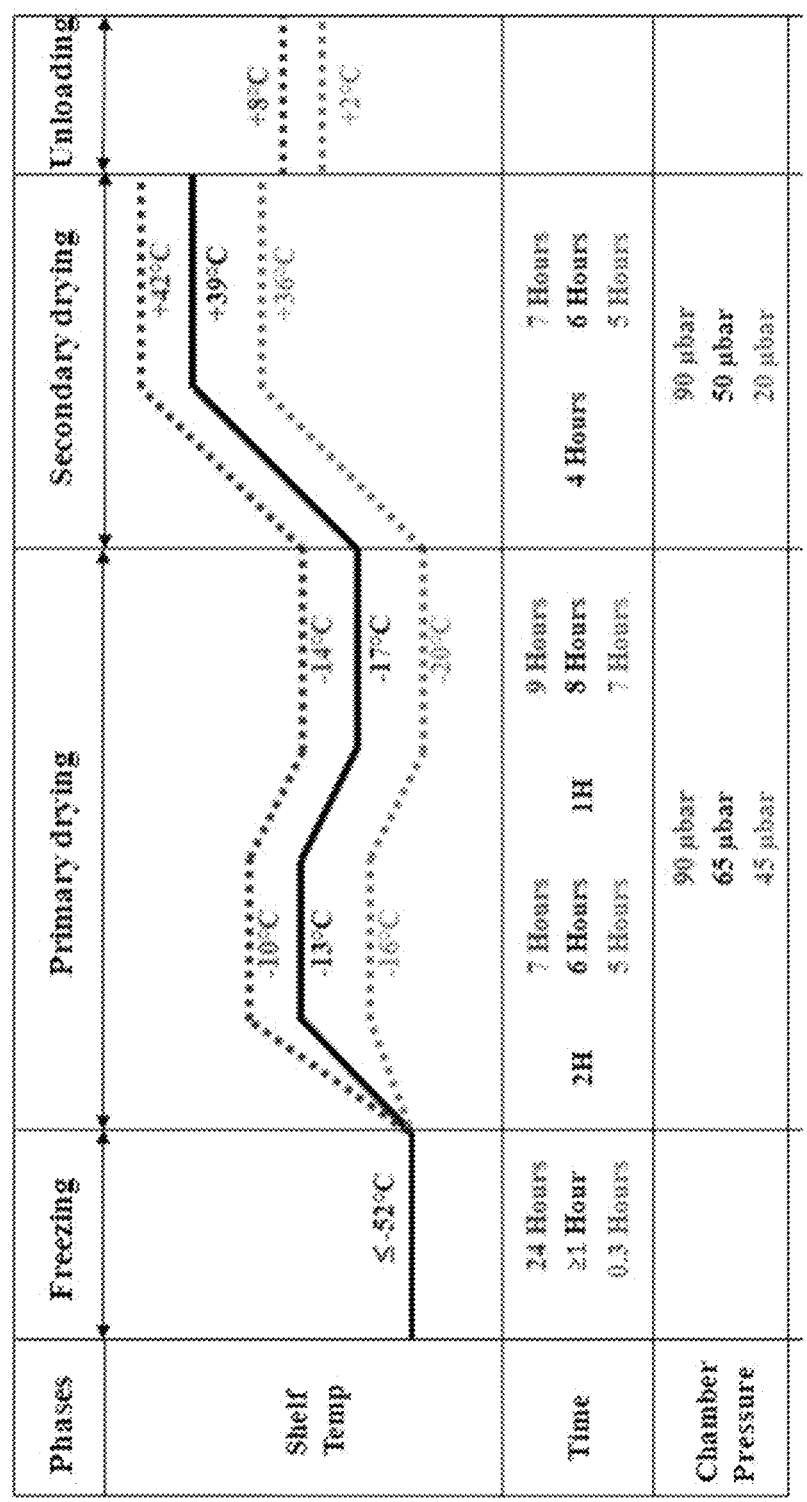

Figure 4-B
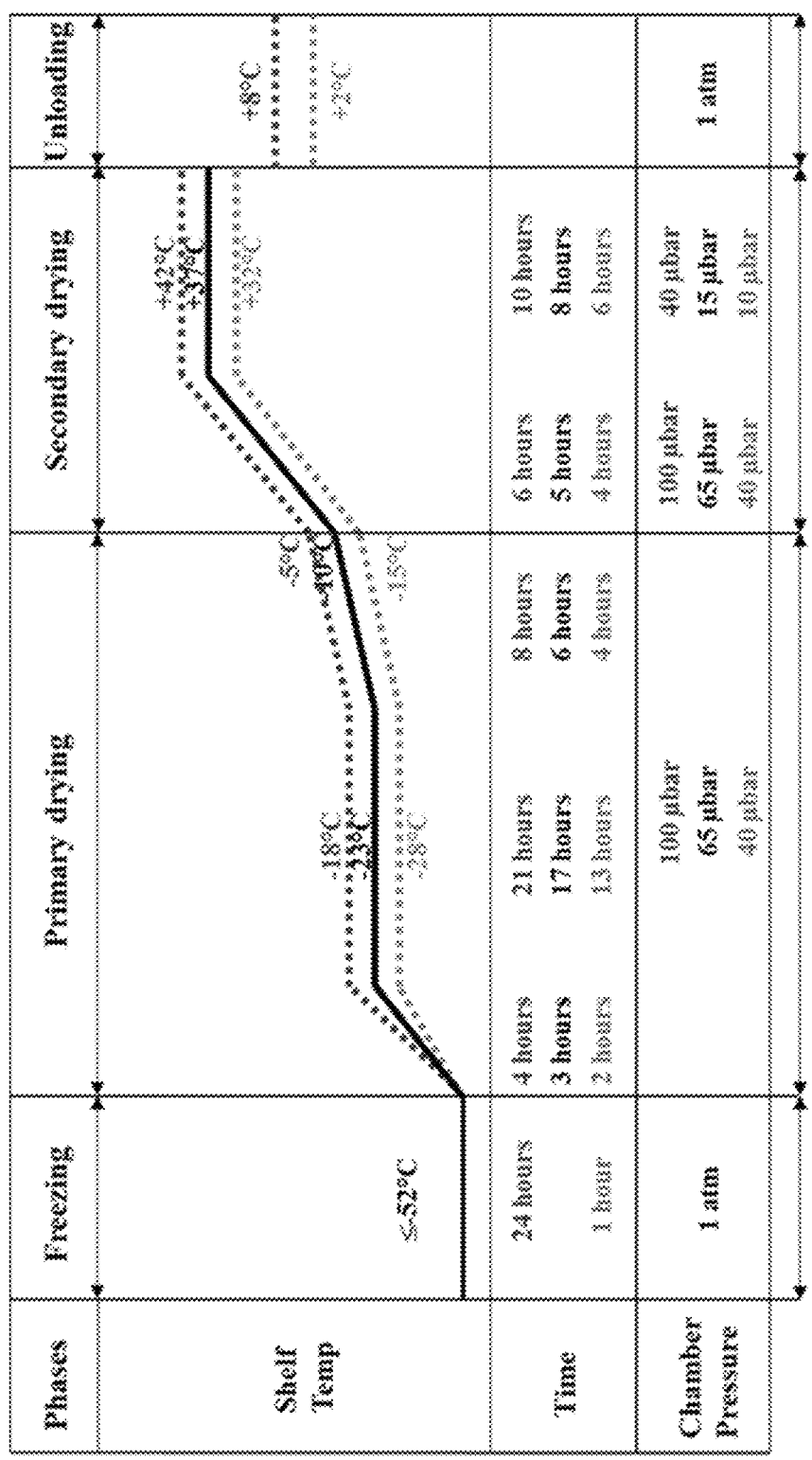

Figure 5-A
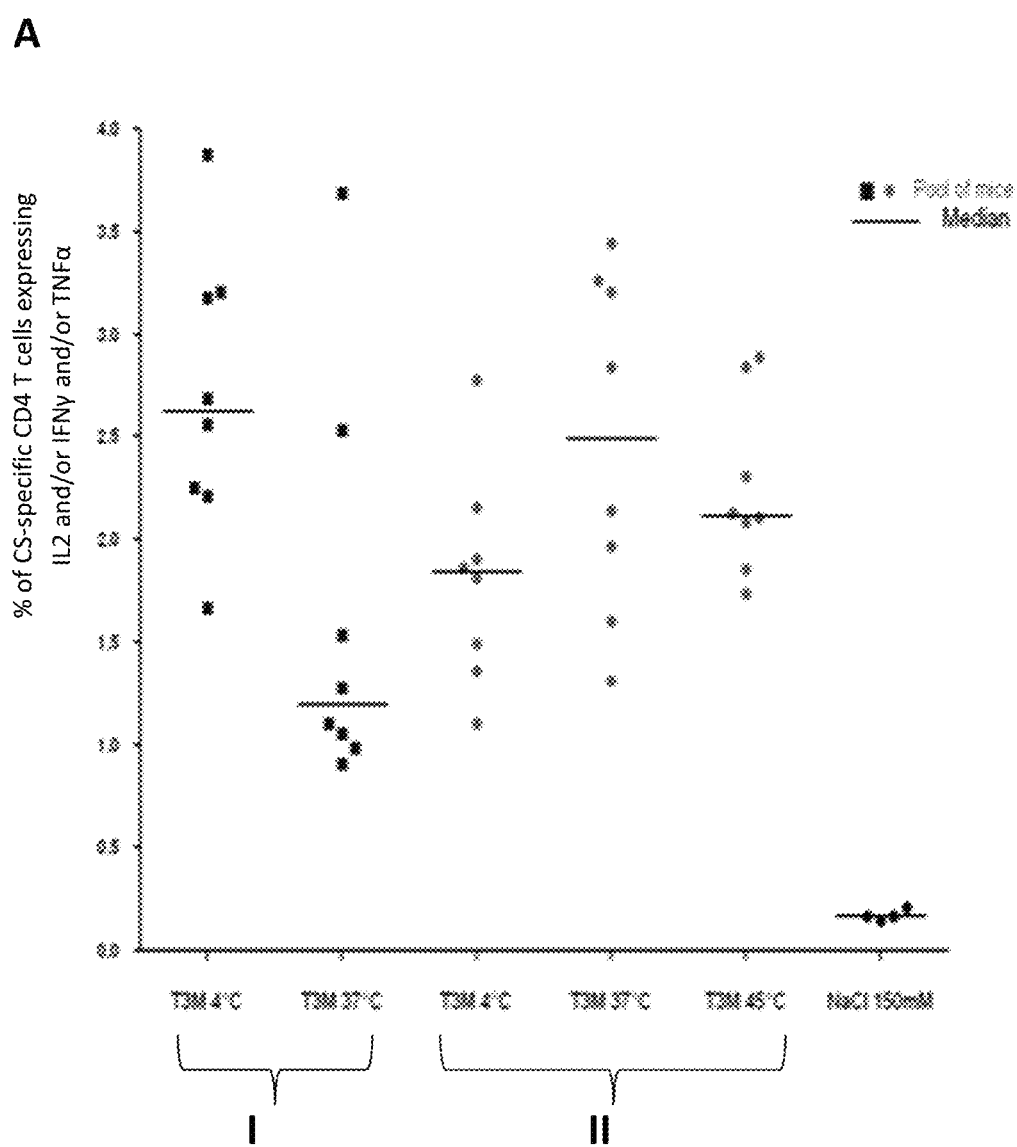

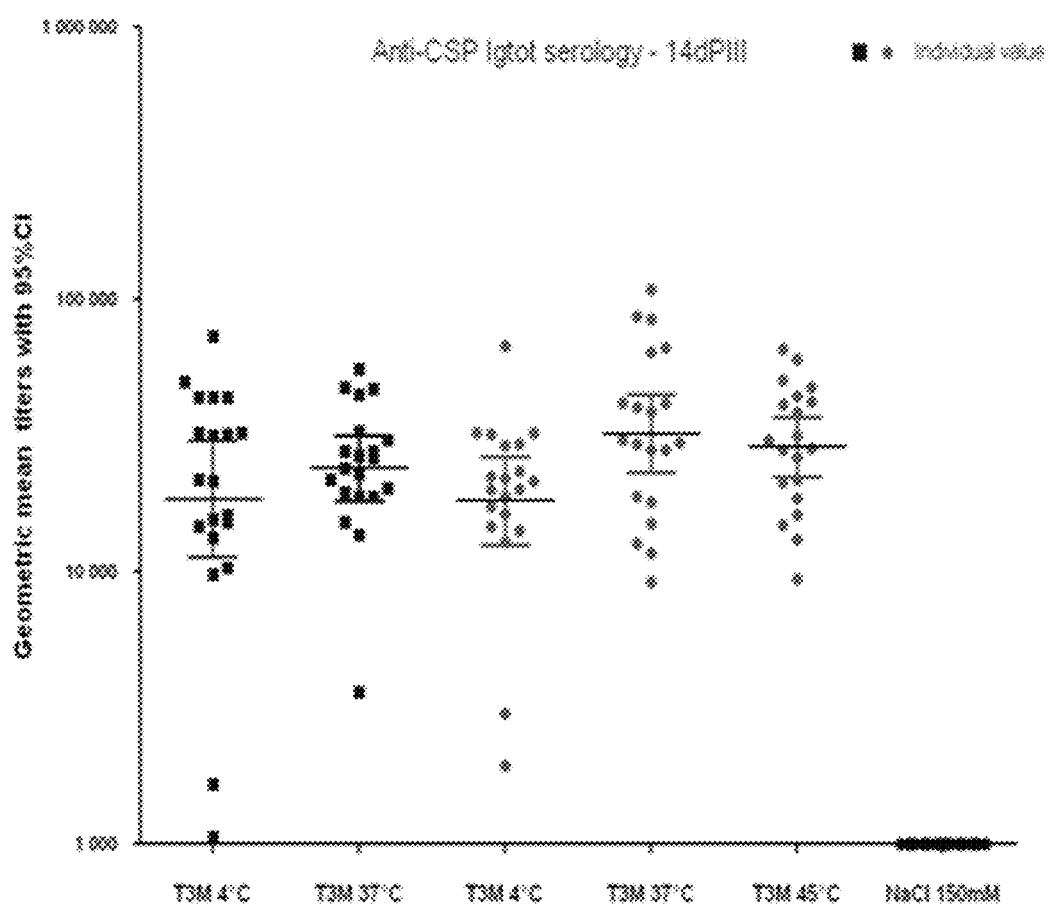
Figure 5-B

Figure 7

SEQ ID NO.: 5

```
  1 MGTVNKPVVG VLMGFGIITG TLRITNPVRA SVLRYDDFHI DEDKLDTNSV YEPYYHSDHA
 61 ESSWVNRGES SRKAYDHNSP YIWPRNDYDG FLENAHEHHG VYNQGRGIDS GERLMQPTQM
121 SAQEDLGDDT GIHVIPTLNG DDRHKIVNVD QRQYGDVFKG DLNPKPQGQR LIEVSVEENH
181 PFTLRAPIQR IYGVRYTETW SFLPSLTCTG DAAPAIQHIC LKHTTCFQDV VVDVDCAENT
241 KEDQLAEISY RFQGKKEADQ PWIVVNTSTL FDELELDPPE IEPGVLKVLR TEKQYLGVYI
301 WNMRGSDGTS TYATFLVTWK GDEKTRNPTP AVTPQPRGAE FHMWNYHSHV FSVGDTFSLA
361 MHLQYKIHEA PFDLLLEWLY VPIDPTCQPM RLYSTCLYHP NAPQCLSHMN SGCTFTSPHL
421 AQRVASTVYQ NCEHADNYTA YCLGISHMEP SFGLILHDGG TTLKFVDTPE SLSGLYVFVV
481 YFNGHVEAVA YTVVSTVDHF VNAIEERGFP PTAGQPPATT KPKEITPVNP GTSPLIRYAA
541 WTGGLA
```

Figure 8
NR
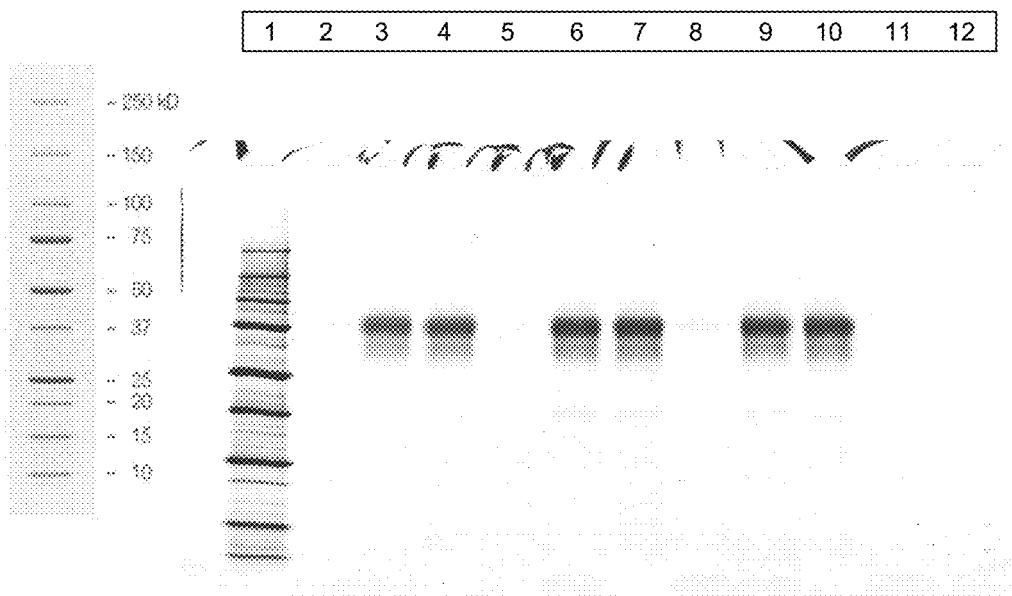
R
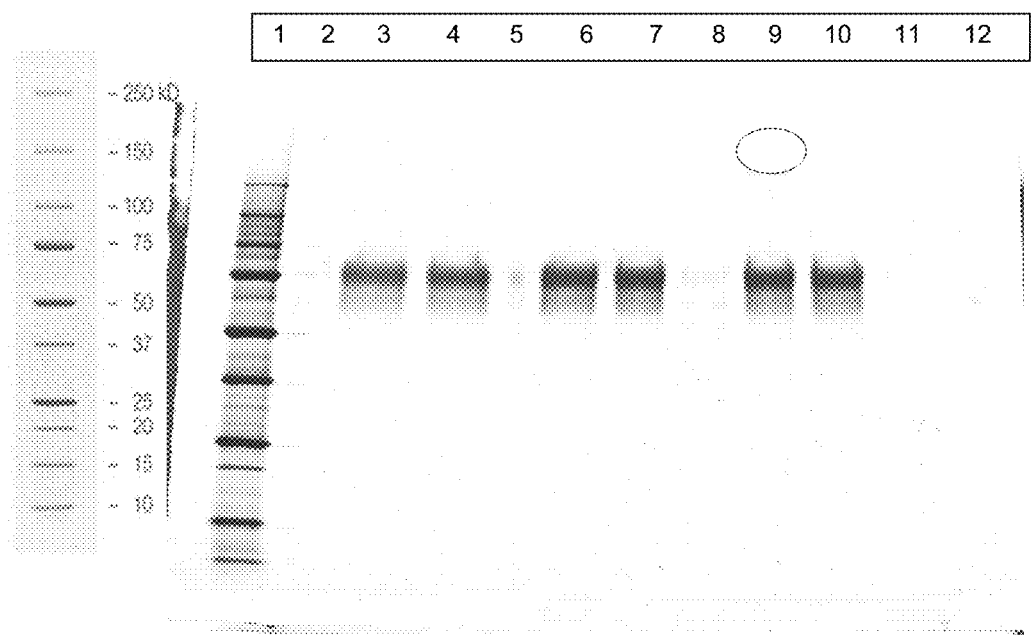

SEQUENCE LISTING

<160> NUMBER OF SEQ ID NOS: 5

<210> SEQ ID NO 1
<211> LENGTH: 391
<212> TYPE: PRT
<213> ORGANISM: M tuberculosis

<400> SEQUENCE: 1

Met Val Asp Phe Gly Ala Leu Pro Pro Glu Ile Asn Ser Ala Arg Met
1               5                   10                  15

Tyr Ala Gly Pro Gly Ser Ala Ser Leu Val Ala Ala Ala Gln Met Trp
            20                  25                  30

-continued

```
Asp Ser Val Ala Ser Asp Leu Phe Ser Ala Ala Ser Ala Phe Gln Ser
        35                  40                  45

Val Val Trp Gly Leu Thr Val Gly Ser Trp Ile Gly Ser Ser Ala Gly
    50                  55                  60

Leu Met Val Ala Ala Ala Ser Pro Tyr Val Ala Trp Met Ser Val Thr
65                  70                  75                  80

Ala Gly Gln Ala Glu Leu Thr Ala Ala Gln Val Arg Val Ala Ala Ala
                85                  90                  95

Ala Tyr Glu Thr Ala Tyr Gly Leu Thr Val Pro Pro Pro Val Ile Ala
            100                 105                 110

Glu Asn Arg Ala Glu Leu Met Ile Leu Ile Ala Thr Asn Leu Leu Gly
        115                 120                 125

Gln Asn Thr Pro Ala Ile Ala Val Asn Glu Ala Glu Tyr Gly Glu Met
    130                 135                 140

Trp Ala Gln Asp Ala Ala Ala Met Phe Gly Tyr Ala Ala Ala Thr Ala
145                 150                 155                 160

Thr Ala Thr Ala Thr Leu Leu Pro Phe Glu Glu Ala Pro Glu Met Thr
                165                 170                 175

Ser Ala Gly Gly Leu Leu Glu Gln Ala Ala Ala Val Glu Glu Ala Ser
            180                 185                 190

Asp Thr Ala Ala Ala Asn Gln Leu Met Asn Asn Val Pro Gln Ala Leu
        195                 200                 205

Gln Gln Leu Ala Gln Pro Thr Gln Gly Thr Thr Pro Ser Ser Lys Leu
    210                 215                 220

Gly Gly Leu Trp Lys Thr Val Ser Pro His Arg Ser Pro Ile Ser Asn
225                 230                 235                 240

Met Val Ser Met Ala Asn Asn His Met Ser Met Thr Asn Ser Gly Val
                245                 250                 255

Ser Met Thr Asn Thr Leu Ser Ser Met Leu Lys Gly Phe Ala Pro Ala
            260                 265                 270

Ala Ala Ala Gln Ala Val Gln Thr Ala Ala Gln Asn Gly Val Arg Ala
        275                 280                 285

Met Ser Ser Leu Gly Ser Ser Leu Gly Ser Ser Gly Leu Gly Gly Gly
    290                 295                 300

Val Ala Ala Asn Leu Gly Arg Ala Ala Ser Val Gly Ser Leu Ser Val
305                 310                 315                 320

Pro Gln Ala Trp Ala Ala Ala Asn Gln Ala Val Thr Pro Ala Ala Arg
                325                 330                 335

Ala Leu Pro Leu Thr Ser Leu Thr Ser Ala Ala Glu Arg Gly Pro Gly
            340                 345                 350

Gln Met Leu Gly Gly Leu Pro Val Gly Gln Met Gly Ala Arg Ala Gly
        355                 360                 365

Gly Gly Leu Ser Gly Val Leu Arg Val Pro Pro Arg Pro Tyr Val Met
    370                 375                 380

Pro His Ser Pro Ala Ala Gly
385                 390

<210> SEQ ID NO 2
<211> LENGTH: 323
<212> TYPE: PRT
<213> ORGANISM: M tuberculosis

<400> SEQUENCE: 2

Ala Pro Pro Ala Leu Ser Gln Asp Arg Phe Ala Asp Phe Pro Ala Leu
1               5                   10                  15
```

```
Pro Leu Asp Pro Ser Ala Met Val Ala Gln Val Gly Pro Gln Val Val
            20                  25                  30

Asn Ile Asn Thr Lys Leu Gly Tyr Asn Asn Ala Val Gly Ala Gly Thr
        35                  40                  45

Gly Ile Val Ile Asp Pro Asn Gly Val Val Leu Thr Asn Asn His Val
    50                  55                  60

Ile Ala Gly Ala Thr Asp Ile Asn Ala Phe Ser Val Gly Ser Gly Gln
65                  70                  75                  80

Thr Tyr Gly Val Asp Val Val Gly Tyr Asp Arg Thr Gln Asp Val Ala
                85                  90                  95

Val Leu Gln Leu Arg Gly Ala Gly Leu Pro Ser Ala Ala Ile Gly
                100                 105                 110

Gly Gly Val Ala Val Gly Glu Pro Val Val Ala Met Gly Asn Ser Gly
            115                 120                 125

Gly Gln Gly Gly Thr Pro Arg Ala Val Pro Gly Arg Val Val Ala Leu
        130                 135                 140

Gly Gln Thr Val Gln Ala Ser Asp Ser Leu Thr Gly Ala Glu Glu Thr
145                 150                 155                 160

Leu Asn Gly Leu Ile Gln Phe Asp Ala Ala Ile Gln Pro Gly Asp Ser
                165                 170                 175

Gly Gly Pro Val Val Asn Gly Leu Gly Gln Val Val Gly Met Asn Thr
            180                 185                 190

Ala Ala Ser Asp Asn Phe Gln Leu Ser Gln Gly Gly Gln Gly Phe Ala
        195                 200                 205

Ile Pro Ile Gly Gln Ala Met Ala Ile Ala Gly Gln Ile Arg Ser Gly
    210                 215                 220

Gly Gly Ser Pro Thr Val His Ile Gly Pro Thr Ala Phe Leu Gly Leu
225                 230                 235                 240

Gly Val Val Asp Asn Asn Gly Asn Gly Ala Arg Val Gln Arg Val Val
                245                 250                 255

Gly Ser Ala Pro Ala Ala Ser Leu Gly Ile Ser Thr Gly Asp Val Ile
            260                 265                 270

Thr Ala Val Asp Gly Ala Pro Ile Asn Ser Ala Thr Ala Met Ala Asp
        275                 280                 285

Ala Leu Asn Gly His His Pro Gly Asp Val Ile Ser Val Thr Trp Gln
    290                 295                 300

Thr Lys Ser Gly Gly Thr Arg Thr Gly Asn Val Thr Leu Ala Glu Gly
305                 310                 315                 320

Pro Pro Ala

<210> SEQ ID NO 3
<211> LENGTH: 723
<212> TYPE: PRT
<213> ORGANISM: M tuberculosis

<400> SEQUENCE: 3

Met Thr Ala Ala Ser Asp Asn Phe Gln Leu Ser Gln Gly Gly Gln Gly
1               5                   10                  15

Phe Ala Ile Pro Ile Gly Gln Ala Met Ala Ile Ala Gly Gln Ile Arg
            20                  25                  30

Ser Gly Gly Gly Ser Pro Thr Val His Ile Gly Pro Thr Ala Phe Leu
        35                  40                  45

Gly Leu Gly Val Val Asp Asn Asn Gly Asn Gly Ala Arg Val Gln Arg
    50                  55                  60
```

-continued

```
Val Val Gly Ser Ala Pro Ala Ser Leu Gly Ile Ser Thr Gly Asp
 65                  70                  75                  80

Val Ile Thr Ala Val Asp Gly Ala Pro Ile Asn Ser Ala Thr Ala Met
                 85                  90                  95

Ala Asp Ala Leu Asn Gly His His Pro Gly Asp Val Ile Ser Val Thr
                100                 105                 110

Trp Gln Thr Lys Ser Gly Gly Thr Arg Thr Gly Asn Val Thr Leu Ala
                115                 120                 125

Glu Gly Pro Pro Ala Glu Phe Met Val Asp Phe Gly Ala Leu Pro Pro
                130                 135                 140

Glu Ile Asn Ser Ala Arg Met Tyr Ala Gly Pro Gly Ser Ala Ser Leu
145                 150                 155                 160

Val Ala Ala Ala Gln Met Trp Asp Ser Val Ala Ser Asp Leu Phe Ser
                165                 170                 175

Ala Ala Ser Ala Phe Gln Ser Val Val Trp Gly Leu Thr Val Gly Ser
                180                 185                 190

Trp Ile Gly Ser Ser Ala Gly Leu Met Val Ala Ala Ser Pro Tyr
                195                 200                 205

Val Ala Trp Met Ser Val Thr Ala Gly Gln Ala Glu Leu Thr Ala Ala
210                 215                 220

Gln Val Arg Val Ala Ala Ala Tyr Glu Thr Ala Tyr Gly Leu Thr
225                 230                 235                 240

Val Pro Pro Pro Val Ile Ala Glu Asn Arg Ala Glu Leu Met Ile Leu
                245                 250                 255

Ile Ala Thr Asn Leu Leu Gly Gln Asn Thr Pro Ala Ile Ala Val Asn
                260                 265                 270

Glu Ala Glu Tyr Gly Glu Met Trp Ala Gln Asp Ala Ala Ala Met Phe
                275                 280                 285

Gly Tyr Ala Ala Ala Thr Ala Thr Ala Thr Ala Thr Leu Leu Pro Phe
                290                 295                 300

Glu Glu Ala Pro Glu Met Thr Ser Ala Gly Gly Leu Leu Glu Gln Ala
305                 310                 315                 320

Ala Ala Val Glu Glu Ala Ser Asp Thr Ala Ala Asn Gln Leu Met
                325                 330                 335

Asn Asn Val Pro Gln Ala Leu Gln Gln Leu Ala Gln Pro Thr Gln Gly
                340                 345                 350

Thr Thr Pro Ser Ser Lys Leu Gly Gly Leu Trp Lys Thr Val Ser Pro
                355                 360                 365

His Arg Ser Pro Ile Ser Asn Met Val Ser Met Ala Asn Asn His Met
                370                 375                 380

Ser Met Thr Asn Ser Gly Val Ser Met Thr Asn Thr Leu Ser Ser Met
385                 390                 395                 400

Leu Lys Gly Phe Ala Pro Ala Ala Ala Gln Ala Val Gln Thr Ala
                405                 410                 415

Ala Gln Asn Gly Val Arg Ala Met Ser Ser Leu Gly Ser Ser Leu Gly
                420                 425                 430

Ser Ser Gly Leu Gly Gly Gly Val Ala Ala Asn Leu Gly Arg Ala Ala
                435                 440                 445

Ser Val Gly Ser Leu Ser Val Pro Gln Ala Trp Ala Ala Ala Asn Gln
                450                 455                 460

Ala Val Thr Pro Ala Ala Arg Ala Leu Pro Leu Thr Ser Leu Thr Ser
465                 470                 475                 480
```

-continued

```
Ala Ala Glu Arg Gly Pro Gly Gln Met Leu Gly Gly Leu Pro Val Gly
                485                 490                 495
Gln Met Gly Ala Arg Ala Gly Gly Leu Ser Gly Val Leu Arg Val
        500                 505                 510
Pro Pro Arg Pro Tyr Val Met Pro His Ser Pro Ala Ala Gly Asp Ile
        515                 520                 525
Ala Pro Pro Ala Leu Ser Gln Asp Arg Phe Ala Asp Phe Pro Ala Leu
    530                 535                 540
Pro Leu Asp Pro Ser Ala Met Val Ala Gln Val Gly Pro Gln Val Val
545                 550                 555                 560
Asn Ile Asn Thr Lys Leu Gly Tyr Asn Asn Ala Val Gly Ala Gly Thr
                565                 570                 575
Gly Ile Val Ile Asp Pro Asn Gly Val Val Leu Thr Asn Asn His Val
            580                 585                 590
Ile Ala Gly Ala Thr Asp Ile Asn Ala Phe Ser Val Gly Ser Gly Gln
        595                 600                 605
Thr Tyr Gly Val Asp Val Gly Tyr Asp Arg Thr Gln Asp Val Ala
    610                 615                 620
Val Leu Gln Leu Arg Gly Ala Gly Gly Leu Pro Ser Ala Ala Ile Gly
625                 630                 635                 640
Gly Gly Val Ala Val Gly Glu Pro Val Val Ala Met Gly Asn Ser Gly
                645                 650                 655
Gly Gln Gly Gly Thr Pro Arg Ala Val Pro Gly Arg Val Val Ala Leu
            660                 665                 670
Gly Gln Thr Val Gln Ala Ser Asp Ser Leu Thr Gly Ala Glu Glu Thr
        675                 680                 685
Leu Asn Gly Leu Ile Gln Phe Asp Ala Ala Ile Gln Pro Gly Asp Ala
    690                 695                 700
Gly Gly Pro Val Val Asn Gly Leu Gly Gln Val Val Gly Met Asn Thr
705                 710                 715                 720
Ala Ala Ser

<210> SEQ ID NO 4
<211> LENGTH: 725
<212> TYPE: PRT
<213> ORGANISM: M tuberculosis

<400> SEQUENCE: 4

Met His His Thr Ala Ala Ser Asp Asn Phe Gln Leu Ser Gln Gly Gly
1               5                   10                  15
Gln Gly Phe Ala Ile Pro Ile Gly Gln Ala Met Ala Ile Ala Gly Gln
            20                  25                  30
Ile Arg Ser Gly Gly Gly Ser Pro Thr Val His Ile Gly Pro Thr Ala
        35                  40                  45
Phe Leu Gly Leu Gly Val Asp Asn Asn Gly Asn Gly Ala Arg Val
    50                  55                  60
Gln Arg Val Val Gly Ser Ala Pro Ala Ala Ser Leu Gly Ile Ser Thr
65                  70                  75                  80
Gly Asp Val Ile Thr Ala Val Asp Gly Ala Pro Ile Asn Ser Ala Thr
                85                  90                  95
Ala Met Ala Asp Ala Leu Asn Gly His His Pro Gly Asp Val Ile Ser
            100                 105                 110
Val Thr Trp Gln Thr Lys Ser Gly Gly Thr Arg Thr Gly Asn Val Thr
        115                 120                 125
```

-continued

Leu Ala Glu Gly Pro Pro Ala Glu Phe Met Val Asp Phe Gly Ala Leu
            130                 135                 140

Pro Pro Glu Ile Asn Ser Ala Arg Met Tyr Ala Gly Pro Gly Ser Ala
145                 150                 155                 160

Ser Leu Val Ala Ala Gln Met Trp Asp Ser Val Ala Ser Asp Leu
                165                 170                 175

Phe Ser Ala Ala Ser Ala Phe Gln Ser Val Val Trp Gly Leu Thr Val
                180                 185                 190

Gly Ser Trp Ile Gly Ser Ser Ala Gly Leu Met Val Ala Ala Ala Ser
            195                 200                 205

Pro Tyr Val Ala Trp Met Ser Val Thr Ala Gly Gln Ala Glu Leu Thr
210                 215                 220

Ala Ala Gln Val Arg Val Ala Ala Ala Tyr Glu Thr Ala Tyr Gly
225                 230                 235                 240

Leu Thr Val Pro Pro Val Ile Ala Glu Asn Arg Ala Glu Leu Met
                245                 250                 255

Ile Leu Ile Ala Thr Asn Leu Leu Gly Gln Asn Thr Pro Ala Ile Ala
            260                 265                 270

Val Asn Glu Ala Glu Tyr Gly Glu Met Trp Ala Gln Asp Ala Ala Ala
    275                 280                 285

Met Phe Gly Tyr Ala Ala Ala Thr Ala Thr Ala Thr Ala Thr Leu Leu
    290                 295                 300

Pro Phe Glu Glu Ala Pro Glu Met Thr Ser Ala Gly Gly Leu Leu Glu
305                 310                 315                 320

Gln Ala Ala Ala Val Glu Glu Ala Ser Asp Thr Ala Ala Ala Asn Gln
                325                 330                 335

Leu Met Asn Asn Val Pro Gln Ala Leu Gln Gln Leu Ala Gln Pro Thr
                340                 345                 350

Gln Gly Thr Thr Pro Ser Ser Lys Leu Gly Gly Leu Trp Lys Thr Val
            355                 360                 365

Ser Pro His Arg Ser Pro Ile Ser Asn Met Val Ser Met Ala Asn Asn
            370                 375                 380

His Met Ser Met Thr Asn Ser Gly Val Ser Met Thr Asn Thr Leu Ser
385                 390                 395                 400

Ser Met Leu Lys Gly Phe Ala Pro Ala Ala Ala Gln Ala Val Gln
                405                 410                 415

Thr Ala Ala Gln Asn Gly Val Arg Ala Met Ser Ser Leu Gly Ser Ser
                420                 425                 430

Leu Gly Ser Ser Gly Leu Gly Gly Val Ala Ala Asn Leu Gly Arg
            435                 440                 445

Ala Ala Ser Val Gly Ser Leu Ser Val Pro Gln Ala Trp Ala Ala Ala
450                 455                 460

Asn Gln Ala Val Thr Pro Ala Ala Arg Ala Leu Pro Leu Thr Ser Leu
465                 470                 475                 480

Thr Ser Ala Ala Glu Arg Gly Pro Gly Gln Met Leu Gly Gly Leu Pro
                485                 490                 495

Val Gly Gln Met Gly Ala Arg Ala Gly Gly Leu Ser Gly Val Leu
                500                 505                 510

Arg Val Pro Pro Arg Pro Tyr Val Met Pro His Ser Pro Ala Ala Gly
            515                 520                 525

Asp Ile Ala Pro Pro Ala Leu Ser Gln Asp Arg Phe Ala Asp Phe Pro
            530                 535                 540

Ala Leu Pro Leu Asp Pro Ser Ala Met Val Ala Gln Val Gly Pro Gln

-continued

```
            545                 550                 555                 560
        Val Val Asn Ile Asn Thr Lys Leu Gly Tyr Asn Asn Ala Val Gly Ala
                        565                 570                 575
        Gly Thr Gly Ile Val Ile Asp Pro Asn Gly Val Val Leu Thr Asn Asn
                        580                 585                 590
        His Val Ile Ala Gly Ala Thr Asp Ile Asn Ala Phe Ser Val Gly Ser
                        595                 600                 605
        Gly Gln Thr Tyr Gly Val Asp Val Val Gly Tyr Asp Arg Thr Gln Asp
                        610                 615                 620
        Val Ala Val Leu Gln Leu Arg Gly Ala Gly Leu Pro Ser Ala Ala
        625                 630                 635                 640
        Ile Gly Gly Gly Val Ala Val Gly Glu Pro Val Val Ala Met Gly Asn
                        645                 650                 655
        Ser Gly Gly Gln Gly Gly Thr Pro Arg Ala Val Pro Gly Arg Val Val
                        660                 665                 670
        Ala Leu Gly Gln Thr Val Gln Ala Ser Asp Ser Leu Thr Gly Ala Glu
                        675                 680                 685
        Glu Thr Leu Asn Gly Leu Ile Gln Phe Asp Ala Ala Ile Gln Pro Gly
                        690                 695                 700
        Asp Ala Gly Gly Pro Val Val Asn Gly Leu Gly Gln Val Val Gly Met
        705                 710                 715                 720
        Asn Thr Ala Ala Ser
                        725

<210> SEQ ID NO 5
<211> LENGTH: 546
<212> TYPE: PRT
<213> ORGANISM: Varicella Zoster Virus

<400> SEQUENCE: 5

Met Gly Thr Val Asn Lys Pro Val Val Gly Val Leu Met Gly Phe Gly
        1               5                   10                  15
        Ile Ile Thr Gly Thr Leu Arg Ile Thr Asn Pro Val Arg Ala Ser Val
                        20                  25                  30
        Leu Arg Tyr Asp Asp Phe His Ile Asp Glu Asp Lys Leu Asp Thr Asn
                        35                  40                  45
        Ser Val Tyr Glu Pro Tyr Tyr His Ser Asp His Ala Glu Ser Ser Trp
                        50                  55                  60
        Val Asn Arg Gly Glu Ser Ser Arg Lys Ala Tyr Asp His Asn Ser Pro
        65                  70                  75                  80
        Tyr Ile Trp Pro Arg Asn Asp Tyr Asp Gly Phe Leu Glu Asn Ala His
                        85                  90                  95
        Glu His His Gly Val Tyr Asn Gln Gly Arg Gly Ile Asp Ser Gly Glu
                        100                 105                 110
        Arg Leu Met Gln Pro Thr Gln Met Ser Ala Gln Glu Asp Leu Gly Asp
                        115                 120                 125
        Asp Thr Gly Ile His Val Ile Pro Thr Leu Asn Gly Asp Asp Arg His
                        130                 135                 140
        Lys Ile Val Asn Val Asp Gln Arg Gln Tyr Gly Asp Val Phe Lys Gly
        145                 150                 155                 160
        Asp Leu Asn Pro Lys Pro Gln Gly Gln Arg Leu Ile Glu Val Ser Val
                        165                 170                 175
        Glu Glu Asn His Pro Phe Thr Leu Arg Ala Pro Ile Gln Arg Ile Tyr
                        180                 185                 190
```

-continued

```
Gly Val Arg Tyr Thr Glu Thr Trp Ser Phe Leu Pro Ser Leu Thr Cys
        195                 200                 205
Thr Gly Asp Ala Ala Pro Ala Ile Gln His Ile Cys Leu Lys His Thr
    210                 215                 220
Thr Cys Phe Gln Asp Val Val Asp Val Asp Cys Ala Glu Asn Thr
225                 230                 235                 240
Lys Glu Asp Gln Leu Ala Glu Ile Ser Tyr Arg Phe Gln Gly Lys Lys
            245                 250                 255
Glu Ala Asp Gln Pro Trp Ile Val Val Asn Thr Ser Thr Leu Phe Asp
                260                 265                 270
Glu Leu Glu Leu Asp Pro Pro Glu Ile Glu Pro Gly Val Leu Lys Val
            275                 280                 285
Leu Arg Thr Glu Lys Gln Tyr Leu Gly Val Tyr Ile Trp Asn Met Arg
    290                 295                 300
Gly Ser Asp Gly Thr Ser Thr Tyr Ala Thr Phe Leu Val Thr Trp Lys
305                 310                 315                 320
Gly Asp Glu Lys Thr Arg Asn Pro Thr Pro Ala Val Thr Pro Gln Pro
                325                 330                 335
Arg Gly Ala Glu Phe His Met Trp Asn Tyr His Ser His Val Phe Ser
                340                 345                 350
Val Gly Asp Thr Phe Ser Leu Ala Met His Leu Gln Tyr Lys Ile His
            355                 360                 365
Glu Ala Pro Phe Asp Leu Leu Leu Glu Trp Leu Tyr Val Pro Ile Asp
    370                 375                 380
Pro Thr Cys Gln Pro Met Arg Leu Tyr Ser Thr Cys Leu Tyr His Pro
385                 390                 395                 400
Asn Ala Pro Gln Cys Leu Ser His Met Asn Ser Gly Cys Thr Phe Thr
                405                 410                 415
Ser Pro His Leu Ala Gln Arg Val Ala Ser Thr Val Tyr Gln Asn Cys
            420                 425                 430
Glu His Ala Asp Asn Tyr Thr Ala Tyr Cys Leu Gly Ile Ser His Met
    435                 440                 445
Glu Pro Ser Phe Gly Leu Ile Leu His Asp Gly Gly Thr Thr Leu Lys
    450                 455                 460
Phe Val Asp Thr Pro Glu Ser Leu Ser Gly Leu Tyr Val Phe Val Val
465                 470                 475                 480
Tyr Phe Asn Gly His Val Glu Ala Val Ala Tyr Thr Val Val Ser Thr
                485                 490                 495
Val Asp His Phe Val Asn Ala Ile Glu Glu Arg Gly Phe Pro Pro Thr
                500                 505                 510
Ala Gly Gln Pro Pro Ala Thr Thr Lys Pro Lys Glu Ile Thr Pro Val
            515                 520                 525
Asn Pro Gly Thr Ser Pro Leu Ile Arg Tyr Ala Ala Trp Thr Gly Gly
            530                 535                 540
Leu Ala
545
```

DRIED COMPOSITION

The present invention relates to the formulation of immunogenic or vaccine compositions comprising a neutral lipid liposome based adjuvant and an antigen derived from *Mycobacterium tuberculosis* (TB) wherein the composition is suitable for lyophilisation. In particular, the invention relates to lyophilised forms of such immunogenic or vaccine compositions wherein both the immunogen or vaccine antigen and the adjuvant are present in one and the same vial. The invention also relates to the formulation and manufacture of lyophilised forms of such immunogenic or vaccine composition.

BACKGROUND

Tuberculosis (TB) is a chronic infectious disease caused by infection with *Mycobacterium tuberculosis* and other *Mycobacterium* species. It is a major disease in developing countries, as well as an increasing problem in developed areas of the world.

Mtb72f and M72 are fusion protein antigens derived from the *Mycobacterium tuberculosis* proteins Rv1196 and Rv0125. Mtb72f and M72 (described, for example, in international patent applications WO2006/117240, WO2012/080369 and WO2012/080370 which are incorporated herein by reference) or fragments or derivatives thereof are protein antigens of potential benefit for the treatment or prevention of tuberculosis.

Preclinical and clinical investigations have led to M72 being administered in humans in conjunction with the immunostimulants 3-O-deacylated monophosphoryl lipid A (3D-MPL) and QS21 in a liposomal formulation and in a 0,1 month schedule using 10 ug M72 polypeptide, 25 ug 3D-MPL and 25 ug QS21 (Leroux-Roels et al *Vaccine* 2013 31 2196-2206, Montoya et al *J. Clin. Immunol.* 2013 33(8): 1360-1375; Thacher E G et al *AIDS* 2014 28(12):1769-81; Idoko O T et al *Tuberculosis* (*Edinb*) 2014 94(6):564-78; Penn-Nicholson A, et al *Vaccine* 2015 doi:10.1016/j.vaccine.2015.05.088). A candidate vaccine utilising the M72 antigen is currently in a Phase IIB trial (ClinicalTrials.gov Identifier: NCT01755598) to evaluate the protective efficacy of two doses of adjuvanted protein against pulmonary TB, as compared to placebo, in adults aged 18-50 living in TB endemic countries.

The vaccine being tested in this Phase IIB trial is a two vial vaccine with a liquid adjuvant. There remains a need for a simplified formulation of this vaccine.

Christensen et al. (2007) [Biochim. Biophys. Acta 1768 (9):2120-2129—Trehalose preserves DDA/TDB liposomes and their adjuvant effect during freeze-drying.] studied the ability of the disaccharides trehalose and sucrose to stabilise a non-phospholipid-based liposomal adjuvant composed of the cationic dimethyldioctadecylammonium (DDA) and trehalose 6,6'-dibehenate (TDB) upon freeze-drying. Trehalose in concentrations of 211 mM and above was found to protect and preserve DDA/TDB liposomes during freeze-drying, whilst sucrose had to be used in concentrations above 396 mM. The protective effect was not observed in liposomes without TDB.

Ingvarsson et al. (2013) [J. Controlled Release 167:256-264, Designing CAF-adjuvanted dry powder vaccines: Spray drying preserves the adjuvant activity] studied spray-drying of the cationic liposome adjuvant DDA/TDB using mannitol, lactose or trehalose.

Mohammed et al. (2006) [Methods 40(1):30-8, Lyophilisation and sterilisation of liposomal vaccines to produce stable and sterile products] is also concerned with lyophilisation of cationic liposome adjuvanted vaccines. It is highlighted that in order to effectively protect liposomes from fusion the cryoprotectant should be present both internally within the liposome and in the external phase and that the intra and extra-liposomal media should have the same osmolarity. To that end, the protocol disclosed provides for the cryoprotectant to be included in the liposomes during liposome formation. Orr et al. (2014) [J. Control Release, 177:20-6 (published electronically 2013) Elimination of the cold chain dependence of a nanoemulsion adjuvanted vaccine against tuberculosis by lyophilisation] relates to co-lyophilisation of emulsion-based adjuvant and antigen.

WO99/65465 relates to a method for agent entrapment in liposomes in the presence of a sugar.

PCT application no. PCT/EP2016/080814 was recently filed. This application is unpublished and is directed towards the formulation of immunogenic or vaccine compositions comprising neutral lipid liposome based adjuvants, where the composition is suitable for lyophilisation.

SUMMARY OF THE INVENTION

The inventors surprisingly found that neutral lipid liposome based adjuvants can successfully be lyophilised. In addition, the inventors found that neutral lipid liposome based adjuvants can be co-lyophilised together with an antigen derived from *Mycobacterium tuberculosis* (TB). Lyophilising the composition confers thermostability to the composition. Increasing the thermostability of the composition may reduce the need for cold-chain maintenance and the development of vaccines that reduce the need for cold-chain maintenance may reduce the cost and technological hurdles associated with the implementation of new vaccines.

In addition, lyophilising a mixture containing the antigen and the adjuvant allows co-vialing of the adjuvant and antigen in dry form. Co-vialing of adjuvant and antigen might further reduce cost and decrease the logistical and technological hurdles involved in the distribution of vaccines worldwide.

The invention, therefore, provides compositions dried under reduced pressure from a liquid mixture comprising:
(a) an adjuvant which comprises a TLR-4 agonist and a saponin in a liposomal formulation, wherein the liposomes contain a neutral lipid and a sterol,
(b) amorphous sugar, wherein the amorphous sugar is present in an amount of more than 7.5% (w/v) of the liquid mixture, and
(c) an antigen derived from *Mycobacterium tuberculosis*.

The present invention also provides a liquid mixture required to form the above mentioned dried composition.

Preferably, the compositions are dried under reduced pressure by lyophilisation.

The composition is preferably dried to a composition containing less than 5% water, preferably less than 3% water. In some embodiments, the composition may comprise less than 2%, less than 1%, less than 0.5% or less than 0.1% water.

In some embodiments, the liquid mixture dried under reduced pressure comprises at least 8% (w/v %) amorphous sugar. For example, the liquid mixture may comprise at least 9%, or at least 10%, or at least 11%, or at least 12%, or at least 13%, or at least 14%, or at least 15% amorphous sugar. In a preferred embodiment, the liquid mixture may comprise more than 7.5% but no more than 15% amorphous sugar. In another preferred embodiment, the liquid mixture may comprise at least 15% amorphous sugar, for example, 15% w/v amorphous sugar.

The amorphous sugar may be a single amorphous sugar or a mixture of amorphous sugars. For example, the amorphous sugar may comprise one or more disaccharides such as sucrose, trehalose, and lactose, and/or one or more trisaccharides such as raffinose. In preferred embodiments, the amorphous sugar may be trehalose, sucrose or combination of sucrose and trehalose.

In some embodiments, the liquid mixture may comprise more than 7.5% but no more than 15% trehalose, sucrose or combination of sucrose and trehalose. For example, the liquid mixture may comprise at least 10% trehalose, at least 10% sucrose or at least 10% of a combination of sucrose and trehalose. In another preferred embodiment, the liquid mixture comprises at least 15% w/v trehalose, sucrose or combination of sucrose and trehalose. For example, in a preferred embodiment, the mixture contains 15% w/v trehalose, sucrose or combination of sucrose and trehalose (with the combination being the most preferred).

In some embodiments, the liquid mixture may further comprise sodium chloride (NaCl). In such embodiments, the liquid mixture preferably contains a low amount of sodium chloride concentration. In some embodiments, the concentration of sodium chloride in the liquid mixture may be below 50 mM, or below 25 mM, or below 10 mM, or below 5 mM. For example, the sodium chloride concentration may be between 0 and 5 mM, or between 0 and 2.5 mM.

In one preferred embodiment, the liquid mixture contains a relatively high concentration of amorphous sugar, and a relatively low concentration of sodium chloride. For example, the liquid mixture may comprise more than 7.5% amorphous sugar and less than 50 mM sodium chloride. In another embodiment, the liquid mixture may comprise more than 7.5 but no more than 15% (w/v %) amorphous sugar and between 0 and 25 mM sodium chloride. In one preferred embodiment, the liquid mixture may comprise 15% (w/v %) amorphous sugar and between 0 and 25 mM sodium chloride In some embodiments, the conductivity of the liquid mixture is 13 mS/cm or lower. In particular, the the conductivity of the liquid mixture may be 12 mS/cm or lower, for example 10 mS/cm or lower, 8 mS/cm or lower, 6 mS/cm or lower, 4 mS/cm or lower, or 3 mS/cm or lower. In a particular embodiment the conductivity of liquid mixture is 2.5 mS/cm or lower, such as 2.25 mS/cm or lower, or 2.0 mS/cm or lower. In a further specific embodiment, the conductivity of the liquid mixture is 1.5 to 2.5 mS/cm.

The conductivity can be measured using techniques known in the art, for example using a dedicated conductivity meter or other instrument with the capability to measure conductivity. One suitable instrument is the Zetasizer Nano ZS from Malvern Instruments (UK).

In some embodiments, the concentration of salts in the liquid mixture is 130 mM or lower. In particular, the present invention provides liquid mixtures wherein the concentration of salts in said composition is 100 mM or lower, for example 90 mM or lower, 80 mM or lower, 70 mM or lower, 60 mM or lower, 50 mM or lower, or 40 mM or lower. In a particular embodiment the concentration of salts in said mixture is 35 mM or lower, such as 30 mM or lower, or 25 mM or lower. In a further specific embodiment the concentration of salts is 20 to 40 mM, such as 25 to 35 mM.

Suitably, the pH of the liquid mixture is between 6 and 9, for example, between 7 and 9, or between 7 and 8.5, or between 7 and 8. For example, in one embodiment, the pH of the liquid mixture may be around 8, i.e. within 0.5 of a pH of 8. In another embodiment, the liquid mixture may have a pH of 8.

In some embodiments of the invention, the liquid mixture may further comprise a polyol such as sorbitol. The concentration of sorbitol in the liquid mixture may less than 6% (w/v %), or less than 5%, or less than 4%, or less than 3%, (w/v %), or less than 2% or less than 1%. In some embodiments, there may be less than 2.7% sorbitol, for example between 1.1% and 2.7% sorbitol, or between 1.175% and 1.925% sorbitol, or between 1.1% and 1.9%, or between 1.2% and 1.9%. In one embodiment, the liquid mixture comprises less than 1.1% (to one decimal place) of sorbitol. In one embodiment, the liquid mixture comprises less than 1.2% (to one decimal place) of sorbitol.

In some embodiments, there may be at least 5 times amorphous sugar in the liquid mixture than sorbitol (by w/v %). In a more preferred embodiment, there is at least 10 times the w/v % of amorphous sugar than sorbitol in the liquid mixture. For example, there may be at least 20 times the w/v % of amorphous sugar. In some embodiments, the ratio of amorphous sugar to sorbitol in w/v % may be between 5:1 and 20:1.

In some embodiments of the invention, more than 7.5% w/v sugar, preferably at least 15% w/v amorphous sugar (for example, 15% sucrose or a mix of sucrose and trehalose) is used in the liquid mixture, and:
  (1) the liquid mixture is formulated with a pH of around 8, and/or
  (2) low concentrations of NaCl (for example, 0 to 25 mM) are used, and/or
  (3) the mixture contains low amounts of sorbitol (for example, between 0 and 1.925% w/v, preferably between 0 and 1.175 w/v %)

Therefore, in one embodiment, a preferred liquid mixture for colyophylization may comprise:
  (1) 15% w/v amorphous sugar,
  (2) 0 to 25 mM NaCl, and
  (3) 0 to 1.175 w/v % sorbitol,
wherein the liquid mixture has a pH of 8.

The invention also provides a method of making the composition dried under reduced pressure, wherein the method comprises the steps of:
  (i) preparing a liquid mixture comprising:
    (a) a saponin;
    (b) liposomes containing a neutral lipid and a sterol;
    (c) amorphous sugar, wherein the amorphous sugar is present in an amount of more than 7.5% (w/v) of the liquid mixture;
    (d) an antigen derived from *Mycobacterium tuberculosis*;
    (e) a TLR-4 agonist;
    (f) optionally a buffer; and
    (g) optionally a surfactant;
  (ii) drying the liquid mixture provided by step (i) under reduced pressure.

In a preferred embodiment, the drying under step (ii) is done by lyophilisation.

As described above, in a preferred embodiment, the liquid mixture may contain more than 7.5% (w/Vv) but no more than 15% amorphous sugar. As also mentioned above, in another preferred embodiment, the liquid mixture may comprise at least 15% amorphous sugar, for example, 15% w/v amorphous sugar. Therefore, the present invention also provides a method of making the composition dried under reduced pressure, wherein the method comprises the steps of:

(i) preparing a liquid mixture comprising:
 (a) a saponin;
 (b) liposomes containing a neutral lipid and a sterol;
 (c) amorphous sugar, wherein the amorphous sugar is present in an amount of more than 15% (w/v) of the liquid mixture;
 (d) an antigen derived from *Mycobacterium tuberculosis*;
 (e) a TLR-4 agonist;
 (f) optionally a buffer; and
 (g) optionally a surfactant;
(ii) drying the liquid mixture provided by step (i) under reduced pressure.

The present invention also provides liquid mixtures comprising:
 (a) an adjuvant which comprises a TLR-4 agonist and a saponin in a liposomal formulation, wherein the liposomes contain a neutral lipid and a sterol,
 (b) amorphous sugar, wherein the amorphous sugar is present in an amount of more than 7.5% (w/v) of the liquid mixture, and
 (c) an antigen derived from *Mycobacterium tuberculosis*.

The invention also provides a vaccine comprising the liquid mixture.

According to another aspect of the invention, there is method of vaccination comprising:
 (a) taking the composition dried under reduced pressure from a liquid mixture;
 (b) reconstituting the dried composition with an isotonic solution; and
 (c) administering the reconstituting composition to a mammal;
wherein the composition comprises 10 to 75 μg of a TLR-4 agonist, 10 to 75 μg of a saponin and 1 to 50 μg of an antigen derived from *Mycobacterium tuberculosis*.

FIGURES

FIG. 1-A illustrates the freeze-drying cycle used in Example 1. The graph of FIG. 1 shows the time in hours associated with each segment of the graph along the x-axis, temperature in degrees Celsius on the left-hand y-axis, and pressure in Pascale on the right-hand y-axis. The graph shows two traces. One of these traces indicates the changing temperature (starts low and increases) and the other the changing pressure (starts high and decreases) over the course of the lyophilisation cycle.

FIG. 1-B also illustrates the freeze-drying cycle used in Example 1. However, the graph of FIG. 1 only shows a single trace for the changing temperature. Pressure is indicated below the x-axis.

FIGS. 2-A, 2-B and 2-C illustrate the results of visual inspection of the cakes.

FIG. 3 illustrates the amount of aggregation seen with the samples.

FIG. 4-A illustrates with the solid line the freeze-drying cycle used for the samples of Example 2; the dotted lines delineate the process acceptable range for the freeze drying of a vaccine composition comprising RTS,S antigen.

FIG. 4-B illustrates an alternative freeze-drying cycle used for the lyophilisation of vaccine compositions comprising AS01 and antigen, as exemplified in Example 3; the dotted lines delineate the process acceptable range for the freeze drying of a vaccine composition.

FIG. 5 illustrates the preclinical immunogenicity data as obtained in Example 2: A. Anti-CSP cellular immune response; B. Anti-CSP antibodies; I. MOSQUIRIX® (freeze-dried RTS,S reconstituted with liquid AS01); II. Co-lyophilised RTS,S/AS01 reconstituted with 150 mM NaCl.

FIG. 7 illustrates the amino acid sequence of VZV gE as used in Example 3.

FIG. 8 illustrates the SDS-page analysis of integrity of VZV gE before and after lyophilisation under different circumstances in Example 3; NR refers to non-reducing conditions, R refers to reducing conditions, the legend for lanes 1 to 12 is provided in Example 3.

SEQUENCE LISTINGS

Figure 3:
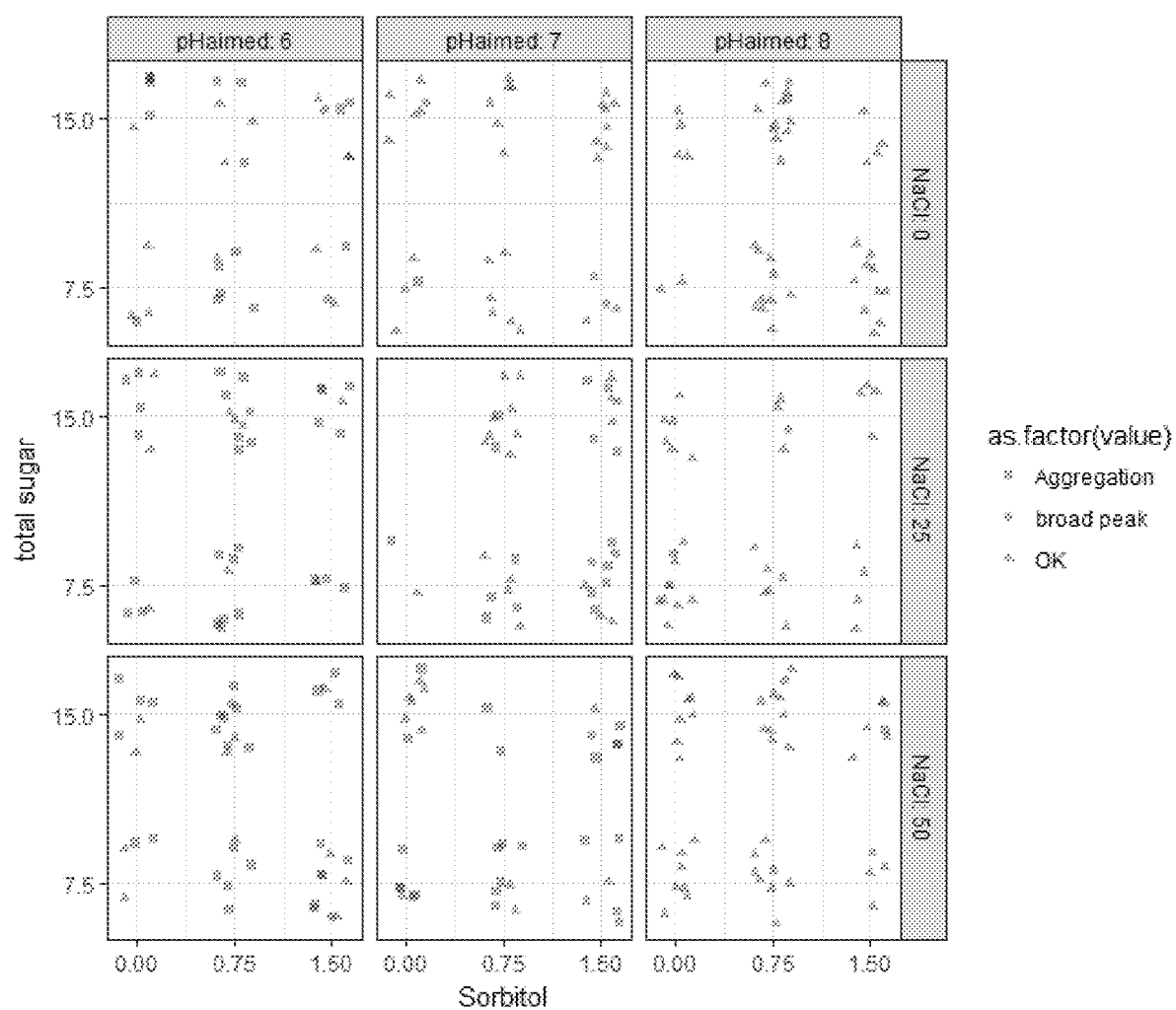

SEQ ID NO: 1 Amino acid sequence for the Rv1196 protein from *Mycobacterium tuberculosis* H37Rv
SEQ ID NO: 2 *Mycobacterium tuberculosis* H37Rv Rv0125 polypeptide sequence
SEQ ID NO: 3 Amino acid sequence for the M72 protein
SEQ ID NO: 4 Amino acid sequence for the M72 protein with two N-terminal His residues

DETAILED DESCRIPTION

The present invention describes the vacuum drying, such as lyophilisation, of a liquid mixture comprising a neutral liposome based adjuvant and an antigen derived from *Mycobacterium tuberculosis*, the formulation of such liquid mixture suitable for lyophilisation as well as methods for lyophilising.

The inventors found that an adjuvant comprising a saponin, a TLR-4 agonist and liposomes, wherein the liposomes are neutral lipid based, can be lyophilised from a mixture further comprising a cryoprotectant selected from amorphous sugars such as sucrose and/or trehalose. In particular, the inventors found that for the claimed liposomal adjuvant composition, the liposomes are not required to be formed in the presence of cryoprotectant in order for the adjuvant to retain its structural integrity and its adjuvant or immune-potentiating properties upon drying or lyophilisation.

Following lyophilisation as described herein, the composition can be stored up to 12, to 24, or to 36 months at 30° C.; up to 6 months, or up to 12 months or 1 year at 37° C.; or, up to three months at 45° C. Suitability for storage can be based on either or both of retention of immunogenicity and retention of structural integrity of the components to an acceptable level. Structural integrity of the liposomes may be assessed by methods such as dynamic light scattering (DLS) measuring the size and polydisperity of the liposomes, or, by electron microscopy for analysis of the structure of the liposomes. In one embodiment the average particle size (by photon correlation spectroscopy) is between 95 and 120 nm, and/or, the polydispersity index (by photon correlation spectroscopy) is not more than 0.2.

From a functional perspective, antigenicity of the antigen can be measured by ELISA. Preclinical assays are available for assessing the overall immunogenicity of the compositions described herein. Immunological assays may quantify a range of responses such as CD4 T cells and/or CD8 T cells.

The present invention further provides a composition as described herein for use in the treatment or prevention of tuberculosis, wherein the composition is an immunogenic composition or a vaccine composition.

The invention also provides methods of therapy or prophylaxis of tuberculosis in an individual in need thereof, comprising the step of providing to said individual an effective amount of an immunogenic or vaccine composition as described herein.

The invention also provides a method for producing a dried composition as described herein, comprising the steps of:
(i) preparing a mixture of a TLR-4 agonist, a saponin, liposomes containing a neutral lipid and a sterol, amorphous sugar, and an antigen derived from *Mycobacterium tuberculosis* (TB); and
(ii) drying the mixture under reduced pressure.

In a further embodiment, the admixed liquid composition of step (i) further comprises one or more components selected from buffers and surfactants. In one embodiment, the admixed liquid composition of step (i) comprises both a buffer and a surfactant.

As used herein, an admixed liquid composition is a composition comprising multiple components, where an isolated component need not be a liquid, but the resulting admixed composition (the mixture) is in liquid form, i.e., the admixed composition is amorphous, flows freely, and is of constant volume under a given pressure.

Definitions

By 'liposomal formulation' is meant the saponin and TLR-4 agonist are formulated with liposomes, or, stated alternatively, presented in a liposome based composition. The liposomes intended for the present invention contain a neutral lipid or consist essentially of neutral lipid, i.e. "neutral liposomes".

By 'neutral lipid' is understood that the overall net charge of the lipid is (approximately) zero. The lipid may therefore be non-ionic overall or may be zwitterionic. In one embodiment the liposomes comprises a zwitterionic lipid. Examples of suitable lipids are phospholipids such as phosphatidylcholine species. In one embodiment the liposomes contain phosphatidylcholine as a liposome forming lipid which is suitably non-crystalline at room temperature. Examples of such non-chrystalline phosphatidylcholine lipids include egg yolk phosphatidylcholine, dioleoyl phosphatidylcholine (DOPC) or dilauryl phosphatidylcholine (DLPC). In a particular embodiment, the liposomes of the present invention contain DOPC, or, consist essentially of DOPC. The liposomes may also contain a limited amount of a charged lipid which increases the stability of the liposome-saponin structure for liposomes composed of saturated lipids. In these cases the amount of charged lipid is suitably 1-20% w/w, preferably 5-10% w/w of the liposome composition. Suitable examples of such charged lipids include phosphatidylglycerol and phosphatidylserine. Suitably, the neutral liposomes will contain less than 5% w/w charged lipid, such as less than 3% w/w or less than 1% w/w.

The liposomes intended for the present invention further comprise a sterol. Suitable sterols include β-sitosterol, stigmasterol, ergosterol, ergocalciferol and cholesterol. In one particular embodiment, the liposomal formulation comprises cholesterol as sterol. These sterols are well known in the art, for example cholesterol is disclosed in the Merck Index, 11th Edn., page 341, as a naturally occurring sterol found in animal fat. The ratio of sterol to phospholipid is 1-50% (mol/mol), suitably 20-25%.

Where the active saponin fraction is QS21, the ratio of QS21:sterol will typically be in the order of 1:100 to 1:1 (w/w), suitably between 1:10 to 1:1 (w/w), and preferably 1:5 to 1:1 (w/w). Suitably excess sterol is present, the ratio of QS21:sterol being at least 1:2 (w/w). In one embodiment, the ratio of QS21:sterol is 1:5 (w/w). In one embodiment, the sterol is cholesterol.

The term 'liposome' is well known in the art and defines a general category of vesicles which comprise one or more lipid bilayers surrounding an aqueous space. Liposomes thus consist of one or more lipid and/or phospholipid bilayers and can contain other molecules, such as proteins or carbohydrates, in their structure. Because both lipid and aqueous phases are present, liposomes can encapsulate or entrap water-soluble material, lipid-soluble material, and/or amphiphilic compounds.

As used herein, a 'neutral liposome based adjuvant' means the adjuvant comprises neutral liposomes for the presentation of the immune-potentiating agents.

As used herein, 'consisting essentially of' means additional components may be present provided they do not alter the overall properties or function.

As used herein, a 'vial' refers to a container suitable for use in packaging, distributing, and using vaccines or immunogenic compositions. A vial may be 'single dose' vial (i.e., a vial containing a quantity of immunogenic or vaccine composition equal to a single dose, such as a single human dose; the specific dosage will vary depending on factors as will be apparent to one skilled in the art, such as the specific composition and the intended recipient). Alternatively, the vial may contain more than one dose ('multi-dose' vial).

As used herein, 'co-vialing' means placing at least two different components, ingredients, or compositions, in a single vial. The vial may be a single-dose vial (containing a single dose of each component, ingredient or composition), or a multi-dose vial.

As used herein, the terms 'mixture' and 'admixture' are used interchangeably.

The terms 'freeze-drying' and 'lyophilising' or 'lyophilisation', and, 'freeze-dried' and 'lyophilised' are used interchangeably and refer to the same process of rapidly freezing a wet substance, followed by dehydration under reduced pressure. Lyophilisation or freeze-drying cycle usually consists of three process phases:
(1) In the first phase of the process a mostly aqueous solution or mixture is frozen.
(2) Subsequently, in the second phase, water is removed by sublimation during primary drying.
(3) In the third phase, non-frozen water is removed by diffusion and desorption during secondary drying.

The term 'glass transition temperature' or 'Tg' is the temperature at which an amorphous solid becomes soft upon heating or brittle upon cooling. The term Tg' refers to the glass transition temperature in the frozen state. The term 'collapse temperature' or 'Tc' refers to the temperature applied during the primary drying and at which an amorphous material softens to the extent that it can no longer support its own structure.

Saponins A suitable saponin for use in the present invention is Quil A and its derivatives. Quil A is a saponin preparation isolated from the South American tree *Quillaja Saponaria Molina* and was first described as having adjuvant activity by Dalsgaard et al. in 1974 ("Saponin adjuvants", Archiv. für die gesamte Virusforschung, Vol. 44, Springer Verlag, Berlin, p 243-254). Purified fragments of Quil A have been isolated by HPLC which retain adjuvant activity without the toxicity associated with Quil A (EP 0

362 278), for example QS7 and QS21 (also known as QA7 and QA21). QS-21 is a natural saponin derived from the bark of *Quillaja saponaria Molina*, which induces CD8+ cytotoxic T cells (CTLs), Th1 cells and a predominant IgG2a antibody response and is a preferred saponin in the context of the present invention. In a suitable form of the present invention, the saponin adjuvant within the immunogenic composition is a derivative of *Saponaria molina* quil A, preferably an immunologically active fraction of Quil A, such as QS-7, QS-17, QS-18 or QS-21, suitably QS-21.

The saponin is provided in its less reactogenic composition where it is quenched with an exogenous sterol, such as cholesterol, and as provided in the liposomal formulation as defined herein above. Several particular forms of less reactogenic compositions wherein QS21 is quenched with an exogenous cholesterol exist. The saponin/sterol is presented in a liposomal formulation structure.

Methods for obtaining saponin/sterol in a liposomal formulation are described in WO 96/33739, in particular Example 1.

TLR4 Agonists

In the present invention the adjuvant comprises a TLR-4 agonist. A suitable example of a TLR-4 agonist is a lipopolysaccharide, suitably a non-toxic derivative of lipid A, particularly monophosphoryl lipid A or more particularly 3-Deacylated monophoshoryl lipid A (3D-MPL).

3D-MPL is sold under the name MPL by GlaxoSmithKline Biologicals N.A. and is referred throughout the document as MPL or 3D-MPL. See, for example, U.S. Pat. Nos. 4,436,727; 4,877,611; 4,866,034 and 4,912,094. 3D-MPL primarily promotes CD4+ T cell responses with an IFN-g (Th1) phenotype. 3D-MPL can be produced according to the methods described in GB 2 220 211 A. Chemically it is a mixture of 3-deacylated monophosphoryl lipid A with 4, 5 or 6 acylated chains. In the compositions of the present invention small particle 3D-MPL may be used to prepare the aqueous adjuvant composition. Small particle 3D-MPL has a particle size such that it may be sterile-filtered through a 0.22 µm filter. Such preparations are described in WO 94/21292. Preferably, powdered 3D-MPL is used to prepare the aqueous adjuvant compositions of the present invention.

Other TLR-4 ligands which can be used are alkyl Glucosaminide phosphates (AGPs) such as those described in WO98/50399 or U.S. Pat. No. 6,303,347 (processes for preparation of AGPs are also described), suitably RC527 or RC529 or pharmaceutically acceptable salts of AGPs as described in U.S. Pat. No. 6,764,840. Some AGPs are TLR-4 agonists, and some are TLR-4 antagonists. Both are thought to be useful as adjuvants.

Other suitable TLR-4 ligands are as described in WO2003/011223 and in WO 2003/099195, such as compound I, compound II and compound III described on pages 4-5 of WO2003/011223 or on pages 3-4 of WO2003/099195 and in particular those compounds described in WO2003/011223 as ER803022, ER803058, ER803732, ER804053, ER804057m ER804058, ER804059, ER804442, ER804680 and ER804764. For example, one suitable TLR-4 ligand is ER804057.

Other TLR-4 ligands which may be of use in the present invention include Glucopyranosyl Lipid Adjuvant (GLA) such as described in WO2008/153541 or WO2009/143457 or the literature articles Coler R N et al. (2011) Development and Characterization of Synthetic Glucopyranosyl Lipid Adjuvant System as a Vaccine Adjuvant. PLoS ONE 6(1): e16333. doi:10.1371/journal.pone.0016333 and Arias M A et al. (2012) Glucopyranosyl Lipid Adjuvant (GLA), a Synthetic TLR4 Agonist, Promotes Potent Systemic and Mucosal Responses to Intranasal Immunization with HIVgp140. PLoS ONE 7(7): e41144. doi:10.1371/journal.pone.0041144. WO2008/153541 or WO2009/143457 are incorporated herein by reference for the purpose of defining TLR-4 ligands which may be of use in the present invention.

In the present invention, the adjuvant comprises both saponin and a TLR4 agonist. In a specific example, the aqueous adjuvant composition comprises QS21 and 3D-MPL. In an alternative embodiment the aqueous adjuvant composition comprises QS21 and GLA.

A TLR-4 ligand such as a lipopolysaccharide, such as 3D-MPL, can be used at amounts between 1 and 100 µg per human dose of the adjuvant composition. 3D-MPL may be used at a level of about 50 µg, such as at least 40 µg, at least 45 µg or at least 49 µg, or, less than 100 µg, less than 80 µg, less than 60 µg, less than 55 µg or less than 51 µg. Examples of suitable ranges are between 40-60 µg, suitably between 45-55 µg or between 49 and 51 µg or 50 µg. In a further embodiment, the human dose of the adjuvant composition comprises 3D-MPL at a level of about 25 µg, such as at least 20 µg, at least 21 µg, at least 22 µg or at least 24 µg, or, less than 30 µg, less than 29 µg, less than 28 µg, less than 27 µg or less than 26 µg. Examples of lower ranges include between 20-30 µg, suitably between 21-29 µg or between 22-28 µg or between 28 and 27 µg or between 24 and 26 µg, or 25 µg.

A saponin, such as QS21, can be used at amounts between 1 and 100 µg per human dose of the adjuvant composition. QS21 may be used at a level of about 50 µg, such as at least 40 µg, at least 45 µg or at least 49 µg, or, less than 100 µg, less than 80 µg, less than 60 µg, less than 55 µg or less than 51 µg. Examples of suitable ranges are between 40-60 µg, suitably between 45-55 µg or between 49 and 51 µg or 50 µg. In a further embodiment, the human dose of the adjuvant composition comprises QS21 at a level of about 25 µg, such as at least 20 µg, at least 21 µg, at least 22 µg or at least 24 µg, or, less than 30 µg, less than 29 µg, less than 28 µg, less than 27 µg or less than 26 µg. Examples of lower ranges include between 20-30 µg, suitably between 21-29 µg or between 22-28 µg or between 28 and 27 µg or between 24 and 26 µg, or 25 µg.

When both a TLR4 agonist and a saponin are present in the adjuvant, then the weight ratio of TLR4 agonist to saponin is suitably between 1:5 to 5:1, suitably 1:1. For example, where 3D-MPL is present at an amount of 50 µg or 25 µg, then suitably QS21 may also be present at an amount of 50 µg or 25 µg per human dose of the adjuvant.

Liposomes

The liposomal formulations as intended for the present invention is defined herein above. WO2013/041572 (also published as US20140234403, incorporated herein by reference in its entirety), in particular examples 3 and 4, describes methods for making a liposome preparation of DOPC liposomes further containing cholesterol and optionally 3D-MPL, for further mixing with QS21, thereby obtaining an adjuvant in accordance with the present invention.

A suitable method described in WO 2013/041572 comprises: (a) producing a lipidic film by (i) dissolving a lipid mix in isopropanol to form a homogeneous mix, and (ii) removing the solvent from the homogeneous mix to form a lipidic film, wherein the lipid mix comprises the lipid and sterol; (b) hydrating the lipidic film with a hydrating solution to form a coarse liposome suspension; (c) reducing size of the coarse liposome suspension produced in step (b) with high shear and high pressure homogenizer to form liposomes; and optionally (d) sterilising the liposomes. Suitably, step (c) comprises steps: (c') pre-homogenising the coarse liposome suspension solution with a high shear mixer, and (c") homogenising the solution produced in step (c') with a high pressure homogeniser.

Antigen

The composition of the present invention comprises an immunogen or antigen derived from *Mycobacterium* spp., such as *Mycobacterium bovis* or *Mycobacterium tuberculosis*, in particular *Mycobacterium tuberculosis* (TB).

Preferably, the antigen derived from *Mycobacterium tuberculosis* is a M72 related antigen.

M72 is a fusion protein derived from two individual antigens: Rv0125 and Rv1196. Rv1196 (described, for example, by the name Mtb39a in Dillon et al *Infection and Immunity* 1999 67(6): 2941-2950) is highly conserved, with 100% sequence identity across H37Rv, C, Haarlem, CDC1551, 94-M4241A, 98-R604INH-RIF-EM, KZN605, KZN1435, KZN4207, KZNR506 strains, the F11 strain having a single point mutation Q30K (most other clinical isolates have in excess of 90% identity to H37Rv). Rv0125 (described, for example, by the name Mtb32a in Skeiky et al *Infection and Immunity* 1999 67(8): 3998-4007) is also highly conserved, with 100% sequence identity across many strains. Full length Rv0125 includes an N-terminal signal sequence which is cleaved to provide the mature protein.

Preferably, the M72 related antigen comprises residues 2-723 of SEQ ID No. 3. For example, the M72 related antigen may comprise (or consist of) SEQ ID No. 3 or comprise (or consist) of SEQ ID No. 4. The proteins recited by SEQ ID No. 3 and SEQ ID No.4 are very similar, the only difference being that SEQ ID No. 4 comprises two additional His residues. Most preferably, the composition comprises the protein of SED ID No. 4.

In other embodiments, the M72 related antigen will comprise, such as consist of, a sequence having at least 70% identity to SEQ ID No. 3, such as at least 80%, in particular at least 90%, especially at least 95%, such as at least 98%, for example at least 99%.

Typical M72 related antigens may comprise, such as consist of, a derivative of SEQ ID No: 3 having a small number of deletions, insertions and/or substitutions. Examples are those having deletions of up to 5 residues at 0-5 locations, insertions of up to 5 residues at 0-5 five locations and substitution of up to 20 residues. Other derivatives of M72 are those comprising, such as consisting of, a fragment of SEQ ID No: 3 which is at least 450 amino acids in length, such as at least 500 amino acids in length, such as at least 550 amino acids in length, such as at least 600 amino acids in length, such as at least 650 amino acids in length or at least 700 amino acids in length. As M72 is a fusion protein derived from the two individual antigens Rv0125 and Rv1196, any fragment of at least 450 residues will comprise a plurality of epitopes from the full length sequence (Skeiky et al J. Immunol. 2004 172:7618-7628; Skeiky Infect. Immun. 1999 67(8):3998-4007; Dillon Infect. Immun. 1999 67(6):2941-2950).

In a further embodiment, the composition may comprise an antigen derived from Rv1196. In this embodiment the antigen may comprise or consist of a sequence having at least 70% identity to SEQ ID No: 1, such as at least 80%, in particular at least 90%, especially at least 95%, for example at least 98%, such as at least 99%. Typical Rv1196 related antigens will comprise (such as consist of) a derivative of SEQ ID No: 1 having a small number of deletions, insertions and/or substitutions. Examples are those having deletions of up to 5 residues at 0-5 locations, insertions of up to 5 residues at 0-5 five locations and substitution of up to 20 residues. Other derivatives of Rv1196 are those comprising (such as consisting of) a fragment of SEQ ID No: 1 which is at least 200 amino acids in length, such as at least 250 amino acids in length, in particular at least 300 amino acids in length, especially at least 350 amino acids in length.

In another embodiment, the composition may comprise an antigen derived from Rv0125. In this embodiment the antigen may comprise, such as consist of, a sequence having at least 70% identity to SEQ ID No: 2, such as at least 80%, in particular at least 90%, especially at least 95%, for example at least 98%, such as at least 99%. Typical Rv0125 related antigens will comprise (such as consist of) a derivative of SEQ ID No: 2 having a small number of deletions, insertions and/or substitutions. Examples are those having deletions of up to 5 residues at 0-5 locations, insertions of up to 5 residues at 0-5 five locations and substitution of up to 20 residues. Other derivatives of Rv0125 are those comprising (such as consisting of) a fragment of SEQ ID No: 2 which is at least 150 amino acids in length, such as at least 200 amino acids in length, in particular at least 250 amino acids in length, especially at least 300 amino acids in length. Particular derivatives of Rv0125 are those comprising (such as consisting of) the fragment of SEQ ID No: 2 corresponding to residues 1-195 of SEQ ID No: 2. Further immunogenic derivatives of Rv0125 are those comprising (such as consisting of) the fragment of SEQ ID No: 2 corresponding to residues 192-323 of SEQ ID No: 2. Particularly preferred Rv0125 related antigens are derivatives of SEQ ID No: 2 wherein at least one (for example one, two or even all three) of the catalytic triad have been substituted or deleted, such that the protease activity has been reduced and the protein more easily produced—the catalytic serine residue may be deleted or substituted (e.g. substituted with alanine) and/or the catalytic histidine residue may be deleted or substituted and/or substituted the catalytic aspartic acid residue may be deleted or substituted. Especially of interest are derivatives of SEQ ID No: 2 wherein the catalytic serine residue has been substituted (e.g. substituted with alanine). Also of interest are Rv0125 related antigens which comprise, such as consist of, a sequence having at least 70% identity to SEQ ID No: 2, such as at least 80%, in particular at least 90%, especially at least 95%, for example at least 98%, such as at least 99% and wherein at least one of the catalytic triad have been substituted or deleted or those comprising, such as consisting of, a fragment of SEQ ID No: 2 which is at least 150 amino acids in length, such as at least 200 amino acids in length, in particular at least 250 amino acids in length, especially at least 300 amino acids in length and wherein at least one of the catalytic triad have been substituted or deleted. Further immunogenic derivatives of Rv0125 are those comprising (such as consisting of) the fragment of SEQ ID No: 2 corresponding to residues 192-323 of SEQ ID No: 2 wherein at least one (for example one, two or even all three) of the catalytic triad have been substituted or deleted. Particular immunogenic derivatives of Rv0125 are those comprising (such as consisting of) the fragment of SEQ ID No: 2 corresponding to residues 1-195 of SEQ ID No: 2 wherein the catalytic serine residue (position 176 of SEQ ID No: 2) has been substituted (e.g. substituted with alanine).

A further antigen that may be employed in accordance with the present invention is the tuberculosis antigen Rv1753 and variants thereof, such as described in WO2010010180, for example a Rv1753 sequence selected from Seq ID Nos: 1 and 2-7 of WO2010010180, in particular Seq ID No: 1. Another antigen of interest in the field of tuberculosis is Rv2386 and variants thereof, such as described in WO2010010179, for example a Rv2386 sequence selected from Seq ID Nos: 1 and 2-7 of WO2010010179, in particular Seq ID No: 1. Other antigens of interest in the field of tuberculosis include Rv3616 and variants thereof, such as described in WO2011092253, for example a natural Rv3616 sequence selected from Seq ID Nos: 1 and 2-7 of WO2011092253 or a modified Rv3616 sequence such as those selected from Seq ID Nos: 161 to 169, 179 and 180 of WO2011092253, in particular Seq ID No: 167. An additional antigen of interest is HBHA, such as described in WO97044463, WO03044048 and WO2010149657.

Other antigens of interest are those comprising (or consisting of): Rv1174, also known as DPV, such as described in SEQ ID No 8 of WO2010010177; Rv1793, also known as MTI or Mtb9.9, such as described in SEQ ID No 10 of WO2010010177; Rv2087, also known as MSL or Mtb9.8, such as described in SEQ ID No 9 of WO2010010177; Rv3616, also known as HTCC1 or Mtb40, such as described in SEQ ID Nos 1 and 2-7 WO2010010177 or SEQ ID Nos 161-169, 179 or 180 of WO2011092253; and/or Rv3874, also known as CFP10 or Tb38.1, such as described in SEQ ID No 9 of WO2010010177; or an immunogenic portion (such as at least 20, 50, 75 or 100 residues therefrom) or variant thereof (such as having at least 70%, 80%, 90% or 95% identity thereto). (WO2010010177 and WO2011092253 are incorporated herein by reference in their entirety).

Tuberculosis antigens are suitably utilised in the form of a polypeptide, but may alternatively be provided in the form of a polynucleotide encoding said polypeptide.

Cryoprotectant

A cryoprotectant suitable for use in the present invention is an amorphous sugar such as one selected from sucrose, trehalose, lactose, raffinose, and combinations thereof. In one embodiment, the cryoprotectant is sucrose or trehalose or a combination thereof. The cryoprotectant may further comprise lyocake structure enhancing sugars such as dextran.

Further Excipients

In one embodiment, the liquid mixture is a substantially aqueous mixture optionally comprising further solvents such as ethanol or isopropanol.

In a further embodiment, a buffer is added to the composition. Suitably, the pH of the liquid mixture is between 6 and 9, for example, between 7 and 9, or between 7 and 8.5, or between 7 and 8.

An appropriate buffer may be selected from acetate, citrate, histidine, maleate, phosphate, succinate, tartrate and TRIS. In one embodiment, the buffer is a phosphate buffer such as Na/Na$_2$PO$_4$, Na/K$_2$PO$_4$ or K/K$_2$PO$_4$.

The buffer can be present in the liquid mixture in an amount of at least 6 mM, at least 10 mM or at least 40 mM. Or, the buffer can be present in the liquid mixture in an amount of less than 100 mM, less than 60 mM or less than 40 mM.

According to specific embodiments, the buffer is a phosphate buffer, present in the liquid mixture in an amount between 6 and 40 mM, such as at about 10 mM. Suitably, the buffer is selected from Na/K$_2$PO$_4$, K/K$_2$PO$_4$ and TRIS. In particular, K/K$_2$PO$_4$ is used as a buffer.

The formulation of a protein antigen for lyophilisation according to the present invention may include a surfactant. Particularly suitable surfactants for use in the present invention include polysorbates, in particular polysorbate 80 (PS80, also referred to as TWEEN® 80), and poloxamer188.

In a further embodiment, the liquid mixture or dried composition contains a limited amount of NaCl, such as less than 60 mM, less than 50 mM, less than 40 mM, less than 30 mM, less than 25 mM or less than 20 mM NaCl in the liquid mixture.

In a further embodiment, the liquid mixture or dried composition contains a limited amount of salts, such as less than 60 mM, less than 50 mM, less than 40 mM, less than 30 mM, less than 25 mM or less than 20 mM NaCl in the liquid mixture.

Tonicity of the composition upon reconstitution can be adjusted using methods know to the skilled person such as by providing sufficient isotonifying agents in the dried composition, such as by reconstituting the dried composition with an at least isotonic solvent. In particular embodiments, tonicity of the reconstituted composition can be adjusted by adding appropriate amounts of NaCl upon reconstitution, e.g. reconstituting the dried composition with saline, or, by increasing the initial amount of cryoprotectant to levels yielding isotonicity upon reconstitution with water for injection. Alternatively the dried composition is reconstituted with an isotonic aqueous solution of a non-ionic isotonifier, e.g. sorbitol.

It is well known that for parenteral administration solutions should have a pharmaceutically acceptable osmolality to avoid cell distortion or lysis. A pharmaceutically acceptable osmolality will generally mean that solutions will have an osmolality which is approximately isotonic or mildly hypertonic. Suitably the compositions of the present invention when reconstituted will have an osmolality of at least 285 mOsm/kg, for example, the osmolality may be in the range of 285 to 900 mOsm/kg.

Osmolality may be measured according to techniques known in the art, such as by the use of a commercially available osmometer, for example the Advanced® Model 2020 available from Advanced Instruments Inc. (USA).

Lyophilisation

As detailed above, the invention also provides a method for producing a dried composition as described herein. For example, in a first embodiment, this method comprises the steps of:

(i) Forming a mixture comprising:
   I. a TLR-4 agonist,
   II. a saponin
   III. liposomes containing a neutral lipid and a sterol,
   IV. amorphous sugar, and
   V. an antigen derived from *Mycobacterium tuberculosis* (TB); and (ii) drying the mixture under reduced pressure.

In a second embodiment, the method for producing the dried composition comprises the steps of:

(i) admixing:
   (a) a liquid liposomal preparation, wherein the liquid liposomal preparation comprises liposomes, said liposomes comprising a neutral lipid and a sterol, and a TLR-4 agonist, wherein the TLR-4 agonist is lipopolysaccharide;
   (b) a saponin;
   (c) amorphous sugar; and
   (d) an antigen derived from *Mycobacterium tuberculosis* (TB); and (ii) drying the mixture under reduced pressure.

In an alternative to this second embodiment, the components of the liquid composition are admixed in a specific order. First, a solution of the amorphous sugar in water is provided, to which (if present) the buffer solution is added. Second the liquid liposomal preparation is added. Third, the saponin component is added. Fourth, (if present) the surfactant is added, and, fifth, the antigen is added. In between certain steps of the process, the mixture may be stirred for some time, e.g. 10 minutes or longer, 15 minutes or longer, 30 minutes or longer, 45 minutes or longer, or, between 15 and 45 minutes. In one embodiments the mixture is stirred after addition of the saponin. In another embodiment, the mixture is stirred for at least 15 minutes after the addition of the surfactant. In yet another embodiment, the mixture is stirred for at least 15 minutes after the addition of the antigen. In a further embodiment, the mixture is stirred for at least 15 minutes after each of the steps of adding the saponin, the surfactant and/or the antigen.

In one embodiment, some or all of the activities in step (i) are performed at room temperature.

Drying under reduced pressure of a liquid mixture as provided under step (ii) can be achieved using different methodologies known in the art. In one embodiment, the drying in step (ii) is done by lyophilisation. As described above, the lyophilisation cycle usually consists of three process phases:

(1) In the first phase, a mostly aqueous solution or mixture is frozen, i.e. "freezing the mixture of step (i)".

(2) Subsequently, water is removed, i.e. "drying of the frozen composition" by sublimation during primary drying.

(3) In the third phase, non-frozen water is removed by diffusion and desorption during secondary drying.

In the lyophilisation of step (ii) the admixed liquid composition of step (i) is frozen prior to the drying by bringing the product temperature below Tg' of the composition. In an embodiment, freezing is achieved by exposing the sample or aqueous mixture to a constant shelf temperature at a freezing temperature which is below Tg'. In an alternative embodiment, the product may be frozen by applying shelf-ramp freezing, i.e. gradually reducing the shelf temperature to a freezing temperature below Tg'. According to embodiments, the freezing temperature is a temperature below Tg' minus 5° C., below Tg' minus 7.5° C., or below Tg' minus 10° C., such as at or below −50° C.

As described above, drying of the frozen composition under reduced pressure as contemplated in the lyophilisation of step (ii) described herein will typically be done in two phases, i.e. primary drying and secondary drying. In an embodiment, drying will include:

primary drying at a temperature below Tc of the product, and, secondary drying at a temperature above Tc of the product and below the Tg of the product.

In one embodiment, the drying step (ii) of the method described herein is completed within 48 hours, within 40 hours, within 36 hours, within 30 hours, or within 28 hours.

The dried composition obtained by the method described may be capable of eliciting an immune response in a subject. The said immune response is in correspondence with the adjuvant and the antigen present in the composition.

In one embodiment, the amorphous sugar is mixed with the liposomal preparation prior to mixing with the saponin. In a further embodiment, the surfactant is admixed prior to the antigen. According to another embodiment, the order of mixture is first mixing the cryoprotectant (i.e. the amorphous sugar) and buffer, followed by the addition of liquid liposomal preparation, saponin, surfactant, and antigen in respective order.

In the description of the method, each of the terms has the same meaning as set forth for the compositions herein.

The following example illustrates the invention.

EXAMPLES

Example 1—Lyophilisation of a TB Antigen Composition

An experiment was designed to test the effectiveness of the lyophilisation of samples containing an adjuvant (which comprises a TLR-4 agonist and a saponin in a liposomal formulation, wherein the liposomes contain a neutral lipid and a sterol), amorphous sugar, and an antigen derived from *Mycobacterium tuberculosis*.

In the experiment the TLR-4 agonist was 3D-MPL, the saponin was QS21, the neutral lipid was dioleoyl phosphatidylcholine (DOPC), the sterol was cholesterol, and the antigen derived from *Mycobacterium tuberculosis* consists of the amino acid sequence of SEQ ID No:4.

In this experiment, samples were prepared with varying amounts of:
amorphous sugar,
salt, and
sorbitol In addition, the pH of the samples was also varied using three different buffers, one with a pH of 6.0, another with a pH of 7.0, and one with a pH of 8.0.

Sample Formulation 360 samples were prepared for lyophilisation. Each of the 360 samples contained:

(1) 25 µg 3D-MPL, 25 µg QS21, 500 µg DOPC, 125 µg cholesterol, 1.175 w/v % sorbitol, 0.625 mM NaCl and 2.5 w/v % $PO_4$. These components were provided by 50 µl of a second solution containing 3D-MPL, QS21, DOPC, cholesterol, sorbitol, NaCl and $PO_4$.

In addition, half of the samples (180) contained:

(2) 25 µg of the M72 antigen. The antigen was provided by adding 14 µl of a solution containing TRIS buffer (pH 7.5) and M72 to each sample.

The other half of the samples (180) contained:

(3) 14 µl of TRIS buffer (pH 7.5) (i.e. no antigen).

In addition, one or more of the following solutions were added to each sample:

(4) 0.5 w/v % aqueous TWEEN® (PS80) solution (5) 50 w/v % aqueous sucrose solution (6) 50 w/v % aqueous trehalose solution (7) 500 mM aqueous NaCl solution (8) 100 mM phosphate buffered saline solution (pH 6.0) ($K/K_2PO_4$)

(9) 100 mM phosphate buffered saline solution (pH 7.0) ($K/K_2PO_4$)

(10) 100 mM TRIS buffer solution (pH 8.0)

The amounts solutions (4) to (10) listed above were varied (together with the amount of added sorbitol, of which 0 w/v %, 0.75 w/v % or 1.5 w/v % were added) to produce 180 different combinations where each combination was formulation both with and without the antigen. The concentrations of each of the different components in the 180 samples are recited as sample numbers 1 to 180 in Table 1 below.

The total volume of each sample was 200 µl. If the volume from the above mentioned solutions totalled less than 200 µl, the volumes were made up to the required amount using water for injection (WFI).

Freeze-Drying

The formulations thus obtained were filled into glass vials (0.200 ml fill volume) and lyophilized by applying the following 40 hour lyophilisation cycle. The glass vials were high throughput glass vials in plate and the samples were formulated by a TECAN automat.

As detailed in FIG. 1-A, the lyophilisation cycle was divided into the following segments:

| Segment | Time (hours) | Temperature (° C.) | Pressure (Pa) | Cumulative time (hours) |
|---|---|---|---|---|
| Segment 1 | 0:00 | −50 | 1 | 00:00 |
| Segment 2 | 1:00 | −50 | 1 | 01:00 |
| Segment 3 | 1:00 | −22 | 0.05 | 02:00 |
| Segment 4 | 28:00 | −22 | 0.05 | 30:00 |
| Segment 5 | 4:00 | 31 | 0.03 | 34:00 |
| Segment 6 | 6:00 | 31 | 0.03 | 40:00 |

In addition, as detailed in FIG. 1-B, the lyophilisation cycle comprised the following stages:

| Stage | Total time in the stage (hours) | Temperature (° C.) | Pressure (Pa) | Cumulative time (hours) |
|---|---|---|---|---|
| Stage 1 | 1:00 | −50 | 1 | 01:00 |
| Stage 2 | 1:00 | From −50 to −22 | 1 | 02:00 |
| Stage 3 | 28:00 | −22 | 0.05 | 30:00 |
| Stage 4 | 4:00 | From −22 to 31 | 0.05 | 34:00 |
| Stage 5 | 6:00 | 31 | 0.03 | 40:00 |

Evaluation

Several aspects were assessed to evaluate the thermal stability of the samples. All measurements were performed at T0 (i.e. just after lyophilisation:

1. Visual Aspect of the Cakes:

The cakes were inspected by eye and with AxioVision (imaging software produced by Zeiss Germany) immediately after the samples had been lyophilised to see if they had collapsed or melted. Table 1 below details these results.

If a cake was considered to have collapsed or melted, this was recorded as "ko" in the results. If no collapse or retraction was observed in the cake, this is indicated as "PASS" in the table. If the appearance of the cake suggested no melting or collapse but the observation was decided not to be entirely conclusive, "PASS . . . " was instead recorded in the table.

The data indicate that the probability of obtaining a good colyophylization is lower when low levels of sugars are used, and that may even decrease further when combined with higher levels of sorbitol and NaCl.

TABLE 1

| | Compositions | | | | | | | | Visual Inspection | |
|---|---|---|---|---|---|---|---|---|---|---|
| Sample Number | TWEEN® (PS 80) w/v % | Sucrose w/v % | Trehalose w/v % | NaCl mM | PO4 6.0 mM | PO4 7.0 mM | TRIS 8.0 mM | Sorbitol w/v % | Sample with no antigen | Sample with 25 μg of the M72 antigen |
| 1 | | 0 | 30 | 0 | 0 | 0 | 0 | 0 | PASS | PASS . . . |
| 2 | 0.025 | 7.5 | 0 | 0 | 0 | 0 | 10 | 0.75 | PASS . . . | PASS . . . |
| 3 | 0.025 | 7.5 | 7.5 | 0 | 0 | 0 | 10 | 0.75 | PASS | PASS . . . |
| 4 | 0.025 | 3.75 | 3.75 | 50 | 0 | 10 | 0 | 1.5 | ko | ko |
| 5 | 0.025 | 0 | 15 | 0 | 10 | 0 | 0 | 0 | PASS | PASS |
| 6 | 0.025 | 3.75 | 3.75 | 50 | 10 | 0 | 0 | 1.5 | ko | ko |
| 7 | 0.025 | 15 | 0 | 50 | 10 | 0 | 0 | 0 | ko | PASS |
| 8 | 0.025 | 15 | 0 | 0 | 0 | 10 | 0 | 0 | PASS | PASS |
| 9 | 0.025 | 7.5 | 0 | 50 | 0 | 0 | 10 | 0 | ko | ko |
| 10 | 0.025 | 15 | 0 | 25 | 0 | 10 | 0 | 0.75 | PASS | PASS |
| 11 | 0.025 | 7.5 | 0 | 50 | 0 | 0 | 10 | 0 | ko | ko |
| 12 | 0.025 | 15 | 0 | 50 | 0 | 10 | 0 | 0 | PASS | PASS |
| 13 | | 0 | 30 | 0 | 0 | 0 | 0 | 0 | PASS | PASS |
| 14 | 0.025 | 0 | 15 | 50 | 0 | 0 | 10 | 1.5 | PASS . . . | PASS |
| 15 | 0.025 | 3.75 | 3.75 | 25 | 0 | 10 | 0 | 0.75 | ko | ko |
| 16 | 0.025 | 7.5 | 7.5 | 25 | 0 | 10 | 0 | 0.75 | ko | PASS |
| 17 | 0.025 | 3.75 | 3.75 | 25 | 10 | 0 | 0 | 0.75 | ko | ko |
| 18 | 0.025 | 15 | 0 | 25 | 10 | 0 | 0 | 0.75 | ko | ko |
| 19 | 0.025 | 7.5 | 7.5 | 50 | 10 | 0 | 0 | 1.5 | PASS | PASS |
| 20 | 0.025 | 0 | 7.5 | 25 | 10 | 0 | 0 | 1.5 | ko | ko |
| 21 | 0.025 | 3.75 | 3.75 | 0 | 0 | 10 | 0 | 0.75 | ko | PASS |
| 22 | 0.025 | 7.5 | 0 | 0 | 0 | 0 | 10 | 1.5 | ko | ko |
| 23 | 0.025 | 0 | 7.5 | 50 | 0 | 0 | 10 | 0 | ko | PASS |
| 24 | 0.025 | 7.5 | 0 | 25 | 0 | 10 | 0 | 1.5 | ko | ko |
| 25 | 0.025 | 7.5 | 0 | 50 | 0 | 10 | 0 | 0 | ko | ko |
| 26 | 0.025 | 15 | 0 | 0 | 10 | 0 | 0 | 1.5 | ko | PASS |
| 27 | 0.025 | 7.5 | 0 | 50 | 0 | 0 | 10 | 1.5 | ko | ko |
| 28 | 0.025 | 7.5 | 7.5 | 0 | 0 | 0 | 10 | 1.5 | PASS | PASS |
| 29 | | 0 | 30 | 0 | 0 | 0 | 0 | 0 | PASS . . . | PASS . . . |
| 30 | 0.025 | 7.5 | 0 | 0 | 0 | 0 | 10 | 0.75 | ko | ko |
| 31 | 0.025 | 7.5 | 0 | 25 | 0 | 0 | 10 | 0 | ko | ko |
| 32 | 0.025 | 7.5 | 0 | 50 | 10 | 0 | 0 | 0.75 | ko | ko |
| 33 | 0.025 | 7.5 | 0 | 0 | 0 | 10 | 0 | 0 | ko | ko |
| 34 | 0.025 | 0 | 7.5 | 50 | 0 | 0 | 10 | 0.75 | ko | ko |
| 35 | 0.025 | 7.5 | 7.5 | 50 | 0 | 0 | 10 | 1.5 | ko | ko |
| 36 | 0.025 | 0 | 15 | 50 | 0 | 10 | 0 | 1.5 | ko | ko |
| 37 | 0.025 | 7.5 | 0 | 0 | 10 | 0 | 0 | 0.75 | ko | ko |

TABLE 1-continued

| | Compositions | | | | | | | | Visual Inspection | |
|---|---|---|---|---|---|---|---|---|---|---|
| Sample Number | TWEEN ® (PS 80) w/v % | Sucrose w/v % | Trehalose w/v % | NaCl mM | PO4 6.0 mM | PO4 7.0 mM | TRIS 8.0 mM | Sorbitol w/v % | Sample with no antigen | Sample with 25 µg of the M72 antigen |
| 38 | 0.025 | 15 | 0 | 50 | 0 | 10 | 0 | 1.5 | ko | ko |
| 39 | 0.025 | 0 | 15 | 0 | 0 | 0 | 10 | 0 | PASS . . . | ko |
| 40 | 0.025 | 7.5 | 0 | 50 | 0 | 10 | 0 | 0 | ko | ko |
| 41 | 0.025 | 15 | 0 | 0 | 0 | 0 | 10 | 0.75 | ko | ko |
| 42 | 0.025 | 7.5 | 0 | 25 | 10 | 0 | 0 | 0 | ko | ko |
| 43 | 0.025 | 3.75 | 3.75 | 50 | 0 | 10 | 0 | 0.75 | ko | ko |
| 44 | 0.025 | 0 | 7.5 | 50 | 0 | 10 | 0 | 0 | PASS . . . | ko |
| 45 | 0.025 | 15 | 0 | 50 | 0 | 0 | 10 | 0.75 | ko | PASS . . . |
| 46 | 0.025 | 0 | 15 | 0 | 10 | 0 | 0 | 1.5 | PASS | ko |
| 47 | | 0 | 30 | 0 | 0 | 0 | 0 | 0 | PASS | ko |
| 48 | 0.025 | 7.5 | 7.5 | 50 | 10 | 0 | 0 | 0.75 | ko | ko |
| 49 | 0.025 | 7.5 | 7.5 | 25 | 10 | 0 | 0 | 0 | PASS . . . | ko |
| 50 | 0.025 | 7.5 | 7.5 | 25 | 0 | 10 | 0 | 1.5 | ko | ko |
| 51 | 0.025 | 7.5 | 7.5 | 0 | 0 | 10 | 0 | 0.75 | PASS . . . | PASS . . . |
| 52 | 0.025 | 15 | 0 | 0 | 0 | 10 | 0 | 0 | ko | PASS . . . |
| 53 | 0.025 | 0 | 7.5 | 0 | 0 | 0 | 10 | 1.5 | ko | Ko |
| 54 | 0.025 | 0 | 15 | 25 | 0 | 0 | 10 | 0 | PASS | PASS |
| 55 | 0.025 | 0 | 15 | 0 | 10 | 0 | 0 | 0.75 | PASS | ko |
| 56 | 0.025 | 0 | 7.5 | 25 | 0 | 10 | 0 | 1.5 | PASS . . . | ko |
| 57 | 0.025 | 0 | 7.5 | 0 | 0 | 0 | 10 | 1.5 | PASS | ko |
| 58 | 0.025 | 0 | 15 | 25 | 10 | 0 | 0 | 1.5 | ko | PASS . . . |
| 59 | 0.025 | 3.75 | 3.75 | 25 | 0 | 10 | 0 | 0.75 | ko | ko |
| 60 | 0.025 | 7.5 | 0 | 0 | 0 | 10 | 0 | 0 | PASS . . . | ko |
| 61 | 0.025 | 15 | 0 | 25 | 0 | 0 | 10 | 0.75 | ko | PASS |
| 62 | 0.025 | 0 | 7.5 | 25 | 0 | 10 | 0 | 0.75 | PASS | PASS |
| 63 | 0.025 | 7.5 | 7.5 | 25 | 10 | 0 | 0 | 0.75 | PASS | PASS |
| 64 | 0.025 | 0 | 15 | 0 | 10 | 0 | 0 | 0 | PASS | PASS |
| 65 | 0.025 | 7.5 | 7.5 | 0 | 0 | 10 | 0 | 1.5 | PASS | PASS |
| 66 | 0.025 | 7.5 | 0 | 0 | 10 | 0 | 0 | 1.5 | ko | ko |
| 67 | 0.025 | 0 | 7.5 | 50 | 10 | 0 | 0 | 0 | PASS | ko |
| 68 | 0.025 | 7.5 | 0 | 50 | 10 | 0 | 0 | 1.5 | ko | ko |
| 69 | 0.025 | 3.75 | 3.75 | 0 | 0 | 10 | 0 | 0.75 | ko | ko |
| 70 | 0.025 | 0 | 7.5 | 25 | 0 | 0 | 10 | 0.75 | PASS . . . | PASS . . . |
| 71 | 0.025 | 0 | 15 | 25 | 0 | 10 | 0 | 0.75 | ko | ko |
| 72 | 0.025 | 0 | 15 | 0 | 0 | 0 | 10 | 0.75 | PASS . . . | PASS . . . |
| 73 | 0.025 | 7.5 | 7.5 | 0 | 10 | 0 | 0 | 0.75 | PASS | PASS |
| 74 | 0.025 | 15 | 0 | 50 | 0 | 0 | 10 | 1.5 | ko | ko |
| 75 | 0.025 | 7.5 | 7.5 | 25 | 0 | 0 | 10 | 0 | PASS | PASS |
| 76 | 0.025 | 7.5 | 7.5 | 50 | 0 | 0 | 10 | 0.75 | ko | ko |
| 77 | 0.025 | 3.75 | 3.75 | 25 | 0 | 10 | 0 | 1.5 | ko | ko |
| 78 | 0.025 | 0 | 15 | 50 | 10 | 0 | 0 | 0.75 | PASS | PASS . . . |
| 79 | 0.025 | 0 | 7.5 | 25 | 0 | 0 | 10 | 0 | ko | ko |
| 80 | 0.025 | 7.5 | 7.5 | 25 | 10 | 0 | 0 | 0.75 | PASS | ko |
| 81 | 0.025 | 0 | 7.5 | 25 | 0 | 10 | 0 | 1.5 | ko | ko |
| 82 | 0.025 | 7.5 | 0 | 50 | 10 | 0 | 0 | 0 | ko | ko |
| 83 | 0.025 | 0 | 7.5 | 25 | 0 | 0 | 10 | 0 | ko | ko |
| 84 | 0.025 | 7.5 | 0 | 0 | 10 | 0 | 0 | 0 | ko | ko |
| 85 | 0.025 | 0 | 15 | 50 | 0 | 10 | 0 | 0 | PASS | ko |
| 86 | 0.025 | 7.5 | 0 | 0 | 0 | 0 | 10 | 1.5 | ko | ko |
| 87 | 0.025 | 3.75 | 3.75 | 0 | 10 | 0 | 0 | 0 | PASS | PASS |
| 88 | 0.025 | 7.5 | 7.5 | 25 | 0 | 0 | 10 | 0.75 | PASS | PASS . . . |
| 89 | 0.025 | 15 | 0 | 25 | 10 | 0 | 0 | 0 | PASS | ko |
| 90 | 0.025 | 0 | 7.5 | 50 | 10 | 0 | 0 | 1.5 | ko | ko |
| 91 | 0.025 | 0 | 15 | 50 | 0 | 10 | 0 | 1.5 | ko | ko |
| 92 | 0.025 | 7.5 | 7.5 | 0 | 10 | 0 | 0 | 1.5 | ko | PASS . . . |
| 93 | 0.025 | 0 | 7.5 | 25 | 0 | 0 | 10 | 1.5 | ko | ko |
| 94 | | 0 | 30 | 0 | 0 | 0 | 0 | 0 | PASS | PASS |
| 95 | 0.025 | 3.75 | 3.75 | 50 | 0 | 10 | 0 | 0.75 | ko | ko |
| 96 | 0.025 | 7.5 | 0 | 50 | 10 | 0 | 0 | 0.75 | ko | ko |
| 97 | 0.025 | 0 | 15 | 50 | 10 | 0 | 0 | 0.75 | PASS . . . | ko |
| 98 | 0.025 | 0 | 15 | 50 | 10 | 0 | 0 | 0 | PASS | ko |
| 99 | | 0 | 30 | 0 | 0 | 0 | 0 | 0 | PASS | PASS |
| 100 | 0.025 | 3.75 | 3.75 | 0 | 0 | 0 | 10 | 0 | Ko | ko |
| 101 | 0.025 | 0 | 7.5 | 25 | 0 | 0 | 10 | 0.75 | PASS . . . | ko |
| 102 | 0.025 | 7.5 | 0 | 25 | 0 | 0 | 10 | 0.75 | ko | ko |
| 103 | 0.025 | 0 | 15 | 50 | 0 | 10 | 0 | 0.75 | ko | PASS . . . |
| 104 | 0.025 | 3.75 | 3.75 | 0 | 0 | 10 | 0 | 1.5 | PASS . . . | ko |
| 105 | 0.025 | 15 | 0 | 0 | 0 | 0 | 10 | 0.75 | PASS . . . | PASS . . . |
| 106 | 0.025 | 7.5 | 0 | 50 | 10 | 0 | 0 | 1.5 | ko | ko |
| 107 | 0.025 | 0 | 15 | 50 | 0 | 0 | 10 | 0.75 | ko | PASS . . . |
| 108 | 0.025 | 15 | 0 | 0 | 0 | 10 | 0 | 1.5 | ko | PASS . . . |
| 109 | 0.025 | 3.75 | 3.75 | 50 | 0 | 0 | 10 | 0.75 | ko | ko |

TABLE 1-continued

| | Compositions | | | | | | | | Visual Inspection | |
|---|---|---|---|---|---|---|---|---|---|---|
| Sample Number | TWEEN ® (PS 80) w/v % | Sucrose w/v % | Trehalose w/v % | NaCl mM | PO4 6.0 mM | PO4 7.0 mM | TRIS 8.0 mM | Sorbitol w/v % | Sample with no antigen | Sample with 25 µg of the M72 antigen |
| 110 | | 0 | 30 | 0 | 0 | 0 | 0 | 0 | PASS | PASS |
| 111 | 0.025 | 15 | 0 | 0 | 0 | 0 | 10 | 0 | ko | PASS . . . |
| 112 | 0.025 | 0 | 15 | 0 | 0 | 10 | 0 | 1.5 | ko | ko |
| 113 | 0.025 | 0 | 7.5 | 0 | 10 | 0 | 0 | 1.5 | ko | ko |
| 114 | 0.025 | 7.5 | 7.5 | 0 | 10 | 0 | 0 | 0 | PASS | PASS |
| 115 | 0.025 | 15 | 0 | 50 | 0 | 0 | 10 | 0.75 | ko | ko |
| 116 | 0.025 | 7.5 | 7.5 | 25 | 0 | 10 | 0 | 1.5 | ko | PASS |
| 117 | 0.025 | 0 | 7.5 | 25 | 0 | 0 | 10 | 0 | ko | PASS . . . |
| 118 | 0.025 | 0 | 15 | 25 | 0 | 10 | 0 | 0.75 | ko | ko |
| 119 | 0.025 | 15 | 0 | 25 | 0 | 10 | 0 | 0.75 | PASS | PASS . . . |
| 120 | 0.025 | 15 | 0 | 50 | 0 | 10 | 0 | 0 | ko | PASS |
| 121 | 0.025 | 15 | 0 | 25 | 0 | 0 | 10 | 1.5 | ko | ko |
| 122 | 0.025 | 7.5 | 0 | 50 | 0 | 0 | 10 | 0 | PASS . . . | ko |
| 123 | 0.025 | 3.75 | 3.75 | 25 | 0 | 10 | 0 | 0.75 | ko | PASS . . . |
| 124 | | 0 | 30 | 0 | 0 | 0 | 0 | 0 | PASS | PASS |
| 125 | 0.025 | 3.75 | 3.75 | 50 | 0 | 0 | 10 | 0.75 | ko | ko |
| 126 | 0.025 | 0 | 15 | 0 | 0 | 10 | 0 | 0.75 | PASS . . . | PASS . . . |
| 127 | 0.025 | 15 | 0 | 25 | 10 | 0 | 0 | 0.75 | ko | PASS . . . |
| 128 | 0.025 | 7.5 | 7.5 | 50 | 0 | 0 | 10 | 0 | PASS . . . | PASS . . . |
| 129 | 0.025 | 7.5 | 0 | 0 | 0 | 10 | 0 | 0.75 | ko | ko |
| 130 | 0.025 | 7.5 | 7.5 | 0 | 0 | 10 | 0 | 1.5 | PASS . . . | PASS . . . |
| 131 | 0.025 | 0 | 7.5 | 0 | 10 | 0 | 0 | 0.75 | PASS . . . | PASS . . . |
| 132 | 0.025 | 15 | 0 | 50 | 10 | 0 | 0 | 0 | ko | PASS . . . |
| 133 | 0.025 | 0 | 15 | 50 | 0 | 10 | 0 | 0 | PASS | PASS . . . |
| 134 | 0.025 | 15 | 0 | 50 | 10 | 0 | 0 | 1.5 | ko | ko |
| 135 | 0.025 | 15 | 0 | 0 | 0 | 0 | 10 | 1.5 | ko | ko |
| 136 | 0.025 | 7.5 | 0 | 25 | 0 | 10 | 0 | 0 | ko | ko |
| 137 | 0.025 | 0 | 7.5 | 50 | 0 | 10 | 0 | 0.75 | ko | ko |
| 138 | 0.025 | 7.5 | 7.5 | 25 | 0 | 0 | 10 | 0 | PASS . . . | PASS . . . |
| 139 | 0.025 | 3.75 | 3.75 | 25 | 10 | 0 | 0 | 0.75 | ko | ko |
| 140 | 0.025 | 0 | 7.5 | 50 | 0 | 10 | 0 | 1.5 | ko | ko |
| 141 | 0.025 | 0 | 7.5 | 25 | 0 | 10 | 0 | 1.5 | ko | ko |
| 142 | 0.025 | 7.5 | 7.5 | 25 | 10 | 0 | 0 | 1.5 | PASS . . . | ko |
| 143 | 0.025 | 0 | 7.5 | 50 | 10 | 0 | 0 | 0.75 | ko | ko |
| 144 | 0.025 | 15 | 0 | 50 | 0 | 0 | 10 | 0.75 | PASS | ko |
| 145 | | 0 | 30 | 0 | 0 | 0 | 0 | 0 | PASS . . . | PASS . . . |
| 146 | 0.025 | 3.75 | 3.75 | 0 | 0 | 0 | 10 | 0.75 | ko | ko |
| 147 | 0.025 | 3.75 | 3.75 | 25 | 10 | 0 | 0 | 0.75 | ko | ko |
| 148 | 0.025 | 7.5 | 7.5 | 25 | 0 | 0 | 10 | 1.5 | PASS | PASS |
| 149 | 0.025 | 0 | 7.5 | 0 | 0 | 0 | 10 | 0.75 | ko | ko |
| 150 | 0.025 | 7.5 | 0 | 25 | 10 | 0 | 0 | 1.5 | ko | ko |
| 151 | 0.025 | 7.5 | 0 | 0 | 0 | 10 | 0 | 1.5 | ko | ko |
| 152 | 0.025 | 3.75 | 3.75 | 50 | 0 | 10 | 0 | 1.5 | ko | ko |
| 153 | 0.025 | 0 | 15 | 50 | 0 | 0 | 10 | 0 | PASS . . . | ko |
| 154 | 0.025 | 7.5 | 0 | 50 | 0 | 0 | 10 | 0.75 | ko | ko |
| 155 | 0.025 | 0 | 7.5 | 50 | 10 | 0 | 0 | 1.5 | ko | ko |
| 156 | 0.025 | 7.5 | 0 | 0 | 10 | 0 | 0 | 0.75 | ko | ko |
| 157 | 0.025 | 7.5 | 7.5 | 0 | 0 | 0 | 10 | 0.75 | PASS | PASS |
| 158 | 0.025 | 7.5 | 7.5 | 50 | 0 | 0 | 10 | 0 | PASS | PASS . . . |
| 159 | 0.025 | 7.5 | 0 | 25 | 10 | 0 | 0 | 0.75 | ko | ko |
| 160 | 0.025 | 0 | 15 | 25 | 10 | 0 | 0 | 0 | PASS | ko |
| 161 | | 0 | 30 | 0 | 0 | 0 | 0 | 0 | PASS . . . | PASS |
| 162 | 0.025 | 3.75 | 3.75 | 50 | 0 | 10 | 0 | 0.75 | ko | ko |
| 163 | 0.025 | 3.75 | 3.75 | 50 | 0 | 0 | 10 | 1.5 | ko | ko |
| 164 | 0.025 | 0 | 15 | 0 | 0 | 0 | 10 | 0.75 | PASS | ko |
| 165 | 0.025 | 3.75 | 3.75 | 25 | 10 | 0 | 0 | 0 | ko | ko |
| 166 | 0.025 | 0 | 15 | 25 | 0 | 10 | 0 | 1.5 | PASS . . . | ko |
| 167 | 0.025 | 3.75 | 3.75 | 0 | 0 | 0 | 10 | 1.5 | ko | ko |
| 168 | 0.025 | 15 | 0 | 25 | 0 | 10 | 0 | 1.5 | ko | ko |
| 169 | 0.025 | 15 | 0 | 25 | 10 | 0 | 0 | 1.5 | ko | ko |
| 170 | 0.025 | 0 | 15 | 25 | 10 | 0 | 0 | 0.75 | PASS | ko |
| 171 | 0.025 | 7.5 | 7.5 | 50 | 10 | 0 | 0 | 0.75 | PASS . . . | PASS . . . |
| 172 | 0.025 | 3.75 | 3.75 | 0 | 0 | 0 | 10 | 0.75 | ko | ko |
| 173 | 0.025 | 15 | 0 | 0 | 10 | 0 | 0 | 0.75 | PASS . . . | PASS . . . |
| 174 | 0.025 | 0 | 15 | 50 | 10 | 0 | 0 | 0.75 | ko | ko |
| 175 | 0.025 | 0 | 7.5 | 25 | 0 | 0 | 10 | 1.5 | ko | ko |
| 176 | 0.025 | 0 | 30 | 0 | 0 | 0 | 0 | 0 | PASS . . . | PASS . . . |
| 177 | 0.025 | 15 | 0 | 0 | 0 | 10 | 0 | 0.75 | PASS | PASS . . . |
| 178 | 0.025 | 7.5 | 7.5 | 0 | 0 | 10 | 0 | 0 | PASS . . . | ko |
| 179 | 0.025 | 7.5 | 7.5 | 50 | 0 | 0 | 10 | 0 | PASS | ko |
| 180 | 0.025 | 7.5 | 0 | 25 | 0 | 0 | 10 | 0 | ko | ko |

The results of visual inspection are illustrated in FIGS. 2-A, 2-B and 2-C. As stated above, after the visual inspection, the cake quality was deemed to be either OK or not OK. In FIG. 2, the cakes are shown as a triangle if they were OK, a square if they were not OK, and a circle if the result was unclear ("PASS . . . "). Clusters of cakes that were shown to almost all be OK are circled by a circle with a broken line (i.e. dotted line), and clusters of cakes that were almost all seem to not be OK on visual inspection are surrounded by a circle with a solid, unbroken line.

As can be seen from FIG. 2-A, the combination of an added sorbitol concentration of 1.5% w/v, and an NaCl concentration of 50 mM were found to generally produce cakes that were deemed "ko". FIG. 2-A also shows that liquid formulations containing 15% w/v sugar, 0 mM NaCl, and 0 to 0.75% added sorbitol generally produced cakes that were deemed "OK".

The results of the visual inspection showed that, for these samples comprising 3D-MPL, QS21, DOPC, cholesterol, and an antigen with the amino acid sequence of SEQ ID No:4:

(1) The highest impact to the cake quality seems to be from the total sugar concentration of the sample (i.e. the liquid mixture).
(2) In particular, samples (liquid mixtures) with 15.0 w/v % total sugar (the highest amount used in the samples), seemed to produce the best cakes when judged on visual inspection.
(3) In addition, it was observed that samples with higher concentrations of sorbitol seemed to produce worse cakes. However, if the total sugar concentration used was high, then it was observed that this can counteract the negative effect of sorbitol to some extent.
(4) Also, it was observed that combinations of different sugars may produce better cakes (when judged by visual inspection) than one type of sugar alone.
(5) In addition, the concentration of NaCl appeared to have an impact on cake quality with some of the samples with higher amounts of NaCl appearing to produce worse cakes.
(6) Finally, in this visual inspection, it was observed that pH seemed to have no impact on the quality of the cake formed.

Therefore, better cakes appeared to generally be formed when higher levels of sugars were used in the liquid mixture, and/or when lower levels of sorbitol and/or NaCl were used.

2. pH pH was measured for the samples without the antigen. The samples were first reconstituted with phosphate-buffered saline (PBS) solution with a pH of 6.1. The results are detailed in Table 2.

3. Osmolality

Osmolality was also measured for the samples without the antigen. These results are also given in Table 2.

The acceptable range for osmolality is greater than or equal to 285 mOsm/kg. In addition, the osmolality is preferably below 900 mOsm/kg as compositions with an osmolality above 900 mOsm/kg may cause pain on injection.

In general, reconstituting with water generated a lower osmolality than reconstituting the with the PBS solution with a pH of 6.1.

4. Reconstitution Time

It was found that all cakes reconstituted instantaneously.

5. Haemolytic Activity

In this experiment, the haemolytic activity was measured for the samples without the antigen and these results are given in Table 2.

QS21 lytic activity is assessed on Sheep Red Blood Cells (SRBC). The reaction was performed in a 96 well microplate (125 μl by well). A standard curve of QS21 is first prepared (0-100 μg/ml in DPBS buffer).

13 μl of red blood cells (diluted 10 times in DPBS) were added to each sample. The samples were gently manually mixed and left for 30 minutes at room temperature. After centrifugation (5 minutes 1500 RPM), the optical density of the supernatant is read at 405 nm and the haemolytic activity of the QS21 is determined by comparing to the standard curve.

Whether or not the liposomes have been degraded by the lyophilisation can been determined by examining the haemolytic activity of the lyophilised composition. If the lyophilised composition demonstrates haemolytic activity then this indicates that QS21 has been released by the liposomes. For there to have been no or little haemolytic activity, the QS21 free content must generally be less than 5 to 6 μg/ml (taking into account the variability of the method). In table 2, "OK" means that there was less than this level of free QS21 in the sample, and "ko" means there was more than 5 to 6 μg/ml QS21.

TABLE 2

|   | pH | Osmolality (mOsm/kg) | | Haemolytic Activity | |
|---|---|---|---|---|---|
|   | Sample without antigen reconstituted with PBS | Sample without antigen reconstituted with PBS | Sample without antigen reconstituted with water | Sample without antigen on the day of lyophilisation (T0) | Sample without antigen at T0 + 22 days |
| 1 | 6.051 | 713 | 517 | OK | OK |
| 2 | 6.885 | 636 | 394 | OK | OK |
| 3 | 6.859 | 856 | 624 | OK | OK |
| 4 | 6.307 | 794 | 543 | OK | OK |
| 5 | 6.120 | 817 | 576 | OK | OK |
| 6 | 6.030 | 751 | 559 | OK | OK |
| 7 | 5.981 | 958 | 818 | OK | OK |
| 8 | 6.381 | 871 | 599 | OK | OK |
| 9 | 6.782 | 700 | 440 | OK | OK |
| 10 | 6.311 | 962 | 718 | OK | OK |
| 11 | 6.768 | 698 | 418 | OK | OK |
| 12 | 6.267 | 969 | 757 | OK | OK |
| 13 | 6.066 | 710 | 515 | OK | OK |
| 14 | 6.729 | 976 | 764 | OK | OK |
| 15 | 6.346 | 680 | 458 | OK | OK |
| 16 | 6.300 | 938 | 700 | OK | OK |
| 17 | 6.077 | 680 | 405 | OK | OK |
| 18 | 6.027 | 960 | 745 | OK | OK |
| 19 | 5.963 | 1039 | 878 | OK | OK |
| 20 | 6.056 | 111 | 466 | OK | OK |
| 21 | 6.416 | 633 | 409 | OK | OK |
| 22 | 6.868 | 692 | 428 | OK | OK |
| 23 | 6.774 | 669 | 428 | OK | OK |
| 24 | 6.338 | 727 | 525 | OK | OK |
| 25 | 6.293 | 685 | 553 | OK | OK |
| 26 | 6.107 | 929 | 742 | OK | OK |
| 27 | 6.765 | 740 | 566 | OK | OK |
| 28 | 6.839 | 878 | 691 | OK | OK |
| 29 | 6.075 | 700 | 475 | OK | OK |
| 30 | 6.886 | 640 | 420 | OK | OK |
| 31 | 6.811 | 631 | 487 | OK | OK |
| 32 | 6.027 | 725 | 508 | OK | OK |
| 33 | 6.423 | 597 | 357 | OK | OK |
| 34 | 6.764 | 685 | 472 | OK | OK |
| 35 | 6.718 | 952 | 838 | OK | OK |
| 36 | 6.252 | 980 | 832 | OK | OK |
| 37 | 6.134 | 675 | 440 | OK | OK |
| 38 | 6.237 | 1008 | 841 | OK | OK |
| 39 | 6.851 | 783 | 564 | OK | OK |
| 40 | 6.293 | 687 | 466 | OK | OK |
| 41 | 6.843 | 831 | 685 | OK | OK |

TABLE 2-continued

| | pH | Osmolality (mOsm/kg) | | Haemolytic Activity | |
|---|---|---|---|---|---|
| | Sample without antigen reconstituted with PBS | Sample without antigen reconstituted with PBS | Sample without antigen reconstituted with water | Sample without antigen on the day of lyophilisation (T0) | Sample without antigen at T0 + 22 days |
| 42 | 6.078 | 643 | 444 | OK | OK |
| 43 | 6.346 | 687 | 609 | OK | OK |
| 44 | 6.300 | 657 | 446 | OK | OK |
| 45 | 6.077 | 943 | 786 | OK | OK |
| 46 | 6.027 | 841 | 701 | OK | OK |
| 47 | 5.963 | 677 | 463 | OK | OK |
| 48 | 6.056 | 955 | 805 | OK | OK |
| 49 | 6.011 | 863 | 766 | OK | OK |
| 50 | 6.263 | 1193 | 778 | OK | OK |
| 51 | 6.362 | 878 | 679 | OK | OK |
| 52 | 6.368 | 811 | 651 | OK | OK |
| 53 | 6.863 | 657 | 452 | OK | OK |
| 54 | 6.779 | 801 | 703 | OK | OK |
| 55 | 6.097 | 807 | 774 | OK | OK |
| 56 | 6.321 | 708 | 520 | OK | OK |
| 57 | 6.871 | 651 | 438 | OK | OK |
| 58 | 6.018 | 906 | 788 | OK | OK |
| 59 | 6.322 | 665 | 452 | OK | OK |
| 60 | 6.411 | 593 | 406 | OK | OK |
| 61 | 6.050 | 899 | 859 | OK | OK |
| 62 | 6.041 | 666 | 458 | OK | OK |
| 63 | 6.050 | 882 | 757 | OK | OK |
| 64 | 6.049 | 817 | 608 | OK | OK |
| 65 | 6.041 | 907 | 752 | OK | OK |
| 66 | 6.052 | 669 | 487 | OK | OK |
| 67 | 6.775 | 661 | 468 | OK | OK |
| 68 | 6.314 | 761 | 554 | OK | OK |
| 69 | 6.008 | 619 | 389 | OK | OK |
| 70 | 6.080 | 656 | 429 | OK | OK |
| 71 | 6.338 | 866 | 698 | OK | OK |
| 72 | 6.129 | 816 | 639 | OK | OK |
| 73 | 5.998 | 855 | 665 | OK | OK |
| 74 | 5.985 | 982 | 836 | OK | OK |
| 75 | 6.4 | 884 | 647 | OK | OK |
| 76 | 6.796 | 986 | 772 | OK | OK |
| 77 | 6.283 | 706 | 506 | OK | OK |
| 78 | 6.832 | 898 | 774 | OK | OK |
| 79 | 6.087 | 629 | 398 | OK | OK |
| 80 | 6.74 | 919 | 723 | OK | OK |
| 81 | 6.776 | 709 | 509 | OK | OK |
| 82 | 6.733 | 674 | 461 | OK | OK |
| 83 | 6.32 | 617 | 390 | OK | OK |
| 84 | 5.964 | 592 | 386 | OK | OK |
| 85 | 6.789 | 929 | 715 | OK | OK |
| 86 | 5.995 | 695 | 525 | OK | OK |
| 87 | 6.311 | 590 | 339 | OK | OK |
| 88 | 6.007 | 871 | 729 | OK | OK |
| 89 | 6.795 | 896 | 790 | OK | OK |
| 90 | 6.146 | 752 | 568 | OK | OK |
| 91 | 6.245 | 929 | 859 | OK | OK |
| 92 | 6.905 | 946 | 722 | OK | OK |
| 93 | 6.143 | 712 | 503 | OK | OK |
| 94 | 6.773 | 699 | 487 | OK | OK |
| 95 | 6.022 | 708 | 551 | OK | OK |
| 96 | 5.989 | 715 | 591 | OK | OK |
| 97 | 6.227 | 935 | 850 | OK | OK |
| 98 | 6.077 | 861 | 713 | OK | OK |
| 99 | 6.8 | 684 | 488 | OK | OK |
| 100 | 6.034 | 569 | 340 | OK | OK |
| 101 | 6.271 | 649 | 467 | OK | OK |
| 102 | 5.993 | 682 | 714 | OK | OK |
| 103 | 5.938 | 915 | 766 | OK | OK |
| 104 | 5.947 | 674 | 463 | OK | OK |
| 105 | 6.034 | 851 | 734 | OK | OK |
| 106 | 6.867 | 755 | 593 | OK | OK |
| 107 | 6.795 | 917 | 784 | OK | OK |
| 108 | 6.801 | 933 | 1019 | OK | OK |
| 109 | 6.234 | 742 | 552 | OK | OK |
| 110 | 6.391 | 713 | 511 | OK | OK |
| 111 | 6.836 | 862 | 657 | OK | OK |
| 112 | 5.999 | 944 | 714 | OK | OK |
| 113 | 6.727 | 698 | 470 | OK | OK |
| 114 | 6.348 | 898 | 850 | OK | OK |
| 115 | 6.785 | 985 | 845 | OK | OK |
| 116 | 6.041 | 1063 | 798 | OK | OK |
| 117 | 6.864 | 613 | 399 | OK | OK |
| 118 | 6.351 | 928 | 735 | OK | OK |
| 119 | 6.117 | 900 | 828 | OK | OK |
| 120 | 6.076 | 957 | 994 | OK | OK |
| 121 | 6.033 | 686 | 872 | OK | OK |
| 122 | 6.03 | 626 | 486 | OK | OK |
| 123 | 6.026 | 920 | 452 | OK | OK |
| 124 | 6.03 | 773 | 578 | OK | OK |
| 125 | 6.029 | 807 | 489 | OK | OK |
| 126 | 6.009 | 808 | 758 | OK | OK |
| 127 | 6.031 | 895 | 788 | OK | OK |
| 128 | 6.871 | 858 | 737 | ko | OK |
| 129 | 6.832 | 720 | 403 | OK | OK |
| 130 | 6.268 | 969 | 684 | OK | OK |
| 131 | 6.094 | 676 | 388 | OK | OK |
| 132 | 5.987 | 1006 | 785 | OK | OK |
| 133 | 5.945 | 769 | 741 | OK | OK |
| 134 | 6.353 | 940 | 866 | OK | OK |
| 135 | 6.77 | 649 | 739 | OK | OK |
| 136 | 6.273 | 897 | 425 | OK | OK |
| 137 | 6.758 | 668 | 488 | OK | OK |
| 138 | 6.232 | 896 | 688 | OK | OK |
| 139 | 6.033 | 972 | 448 | OK | OK |
| 140 | 6.719 | 710 | 534 | OK | OK |
| 141 | 6.316 | 614 | 483 | OK | OK |
| 142 | 6.263 | 664 | 742 | OK | OK |
| 143 | 6.031 | 653 | 497 | OK | OK |
| 144 | 5.982 | 710 | 843 | OK | OK |
| 145 | 5.930 | 672 | 503 | OK | OK |
| 146 | 6.019 | 903 | 404 | OK | OK |
| 147 | 6.390 | 740 | 457 | OK | OK |
| 148 | 6.864 | 880 | 761 | OK | OK |
| 149 | 6.763 | 674 | 375 | OK | OK |
| 150 | 6.309 | 648 | 535 | OK | OK |
| 151 | 6.265 | 640 | 490 | OK | OK |
| 152 | 6.074 | 725 | 563 | OK | OK |
| 153 | 6.754 | 596 | 714 | OK | OK |
| 154 | 6.822 | 690 | 521 | OK | OK |
| 155 | 6.039 | 947 | 540 | OK | OK |
| 156 | 6.857 | 926 | 440 | OK | OK |
| 157 | 6.793 | 638 | 681 | OK | OK |
| 158 | 5.984 | 959 | 715 | OK | OK |
| 159 | 6.394 | 763 | 459 | OK | OK |
| 160 | 6.757 | 671 | 628 | OK | OK |
| 161 | 6.707 | 825 | 486 | OK | OK |
| 162 | 6.225 | 639 | 533 | OK | OK |
| 163 | 6.109 | 701 | 547 | OK | OK |
| 164 | 6.221 | 661 | 656 | OK | OK |
| 165 | 6.838 | 931 | 413 | OK | OK |
| 166 | 6.27 | 862 | 746 | OK | OK |
| 167 | 6.826 | 676 | 463 | OK | OK |
| 168 | 6.044 | 948 | 852 | OK | OK |
| 169 | 6.25 | 876 | 936 | OK | OK |
| 170 | 6.273 | 957 | 752 | OK | OK |
| 171 | 6.736 | 887 | 772 | OK | OK |
| 172 | 6.079 | 836 | 414 | OK | OK |
| 173 | 6.026 | 644 | 795 | OK | OK |
| 174 | 5.934 | 841 | 844 | OK | OK |
| 175 | 5.978 | 818 | 545 | OK | OK |
| 176 | 6.255 | 710 | 523 | OK | OK |
| 177 | 6.332 | 705 | 794 | OK | OK |
| 178 | 6.342 | 921 | 667 | OK | OK |
| 179 | 6.858 | 675 | 794 | OK | OK |
| 180 | 6.758 | 595 | 470 | OK | OK |

6. Antigen Content

The antigen content of some of the antigen-containing samples was also measured after lyophilisation. The amount of antigen was quantified after lyophilisation using reverse-phased ultra high performance liquid chromatography (RP UPLC). This showed that there was antigen present after lyophilisation.

7. Aggregation State

The aggregation state of the antigen containing samples after lyophilisation was measured using size-exclusion high performance liquid chromatography (SEC HPLC). These results are given in Table 3 below.

TABLE 3

| Sample Number | Aggregation (SEC HPLC) | |
|---|---|---|
| | % Surface/PB | Aggregation |
| 1 | 1.94 | |
| 2 | 42.46 | |
| 3 | 37.44 | |
| 4 | 28.21 | |
| 5 | 65.69 | |
| 6 | 24.13 | |
| 7 | 42.29 | |
| 8 | 52.51 | |
| 9 | 56.22 | |
| 10 | 40.74 | |
| 11 | 19.51 | |
| 12 | 49.20 | |
| 13 | 35.14 | Aggregation |
| 14 | 39.27 | |
| 15 | 55.18 | Aggregation |
| 16 | 37.23 | |
| 17 | 41.52 | Aggregation |
| 18 | 86.27 | |
| 19 | 83.56 | Aggregation |
| 20 | 30.60 | Aggregation |
| 21 | 54.84 | |
| 22 | 106.11 | OK |
| 23 | 62.83 | |
| 24 | 35.98 | |
| 25 | 57.21 | Aggregation |
| 26 | 80.23 | OK |
| 27 | 95.65 | OK |
| 28 | 63.79 | |
| 29 | 68.74 | |
| 30 | 45.96 | |
| 31 | 92.89 | OK |
| 32 | 52.28 | |
| 33 | 60.94 | Aggregation |
| 34 | 85.57 | OK |
| 35 | 93.35 | OK |
| 36 | 45.12 | Aggregation |
| 37 | 71.09 | Aggregation |
| 38 | 111.09 | broad peak |
| 39 | 103.60 | OK |
| 40 | 45.01 | Aggregation |
| 41 | 107.78 | OK |
| 42 | 39.70 | Aggregation |
| 43 | 60.12 | Aggregation |
| 44 | 35.19 | Aggregation |
| 45 | 66.35 | |
| 46 | 80.57 | Aggregation |
| 47 | 61.68 | |
| 48 | 68.82 | Aggregation |
| 49 | 90.84 | Aggregation |
| 50 | 54.90 | Aggregation |
| 51 | 61.06 | |
| 52 | 99.92 | OK |
| 53 | 77.00 | |
| 54 | 89.37 | OK |
| 55 | 82.55 | Aggregation |
| 56 | 56.79 | Aggregation |
| 57 | 63.50 | |
| 58 | 70.72 | Aggregation |
| 59 | 55.99 | |
| 60 | 61.09 | |

TABLE 3-continued

| Sample Number | Aggregation (SEC HPLC) | |
|---|---|---|
| | % Surface/PB | Aggregation |
| 61 | 78.63 | OK |
| 62 | 93.90 | OK |
| 63 | 95.57 | Broad peak-Aggregation |
| 64 | 93.38 | OK |
| 65 | 104.19 | OK |
| 66 | 95.21 | broad peak |
| 67 | 85.00 | Aggregation |
| 68 | 105.63 | broad peak |
| 69 | 85.69 | OK |
| 70 | 90.30 | OK |
| 71 | 97.57 | OK |
| 72 | 97.57 | OK |
| 73 | 101.50 | OK |
| 74 | 99.24 | Aggregation |
| 75 | 79.25 | OK |
| 76 | 85.96 | broad peak |
| 77 | 60.02 | broad peak |
| 78 | 57.31 | broad peak |
| 79 | 92.97 | OK |
| 80 | 63.66 | |
| 81 | 68.51 | broad peak |
| 82 | 75.68 | OK |
| 83 | 58.95 | broad peak |
| 84 | 74.56 | OK |
| 85 | 39.87 | |
| 86 | 67.82 | |
| 87 | 97.56 | OK |
| 88 | 96.81 | broad peak |
| 89 | 110.04 | OK |
| 90 | 88.66 | OK |
| 91 | 82.86 | broad peak |
| 92 | 87.07 | broad peak |
| 93 | 56.69 | |
| 94 | 64.52 | |
| 95 | 90.40 | Aggregation |
| 96 | 95.49 | Aggregation |
| 97 | 81.94 | Aggregation |
| 98 | 77.96 | Aggregation |
| 99 | 40.46 | |
| 100 | 68.83 | |
| 101 | 78.09 | |
| 102 | 67.55 | |
| 103 | 95.07 | Aggregation |
| 104 | 107.73 | |
| 105 | 81.23 | |
| 106 | 48.22 | Aggregation |
| 107 | 79.66 | |
| 108 | 87.09 | |
| 109 | 113.57 | |
| 110 | 94.81 | |
| 111 | 108.12 | |
| 112 | 105.27 | |
| 113 | | |
| 114 | 108.82 | |
| 115 | 108.03 | |
| 116 | 104.51 | |
| 117 | 109.81 | |
| 118 | 112.11 | |
| 119 | 114.89 | |
| 120 | 96.71 | |
| 121 | 98.01 | |
| 122 | 76.77 | |
| 123 | 76.66 | Aggregation |
| 124 | 79.44 | |
| 125 | 94.35 | |
| 126 | 105.33 | |
| 127 | 100.59 | |
| 128 | 82.20 | |
| 129 | 99.69 | |
| 130 | 85.41 | |
| 131 | 78.43 | Aggregation |
| 132 | 94.00 | Aggregation |
| 133 | 107.68 | Aggregation |
| 134 | 92.40 | Aggregation |
| 135 | 106.65 | OK |
| 136 | 97.93 | OK |

TABLE 3-continued

| Sample Number | % Surface/PB | Aggregation (SEC HPLC) Aggregation |
|---|---|---|
| 137 | 79.51 | Aggregation |
| 138 | 99.01 | OK |
| 139 | 61.53 | Aggregation |
| 140 | 73.77 | Aggregation |
| 141 | 78.86 | Aggregation |
| 142 | 89.52 | Aggregation |
| 143 | 49.82 | Aggregation |
| 144 | 101.66 | OK |
| 145 | 92.38 | OK |
| 146 | 110.90 | OK |
| 147 | 53.46 | Aggregation |
| 148 | 91.05 | OK |
| 149 | 106.91 | OK |
| 150 | 85.34 | Aggregation |
| 151 | 107.02 | broad peak |
| 152 | 82.92 | Aggregation |
| 153 | 114.82 | OK |
| 154 | 116.83 | OK |
| 155 | 34.50 | Aggregation |
| 156 | 79.27 | Aggregation |
| 157 | 106.88 | OK |
| 158 | 99.69 | OK |
| 159 | 73.09 | Aggregation |
| 160 | 82.28 | Aggregation |
| 161 | 94.89 | OK |
| 162 | 90.40 | Aggregation |
| 163 | 84.15 | OK |
| 164 | 90.75 | OK |
| 165 | 63.67 | Aggregation |
| 166 | 98.51 | Aggregation |
| 167 | 88.53 | OK |
| 168 | 89.43 | broad peak |
| 169 | 78.94 | Aggregation |
| 170 | 99.39 | Aggregation |
| 171 | 84.59 | Aggregation |
| 172 | 97.50 | OK |
| 173 | 73.06 | Aggregation |
| 174 | 61.25 | Aggregation |
| 175 | 87.71 | OK |
| 176 | 77.12 | |
| 177 | 82.46 | OK |
| 178 | 86.25 | broad peak |
| 179 | 81.79 | OK |
| 180 | 70.40 | |

The aggregation results are illustrated in FIG. 3. If aggregation was seen for a sample, this is represented as a square on the graph. If there was no aggregation observed, this is shown as a circle.

In terms of aggregation for these samples containing 3D-MPL, QS21, DOPC, cholesterol, and an antigen consisting of the amino acid sequence of SEQ ID No:4., it was observed that:
(1) pH seems affect aggregation. For example:
   a. in this experiment, samples (i.e. liquid mixtures) formulated at pH 8 seem to produce the best results, and
   b. samples formulated at pH 7 also seem fine if the concentration of NaCl is low (or if no NaCl is present).
(2) The amount of added sorbitol does not seem to have much of an effect on the amount of aggregation.
(3) The results also indicate that less aggregation may be observed when the samples have a higher sugar content.

8. Visual Inspection of the Cakes and Aggregation:
Upon analysing the combined results of the visual inspection of the cakes and aggregation, it was found that preferred samples for colyophylization may be produced if higher concentrations of sugar are used in the liquid mixture containing 3D-MPL, QS21, DOPC, cholesterol, and an antigen of the amino acid sequence of SEQ ID No:4 before lyophylization. Preferably, 15% sugar (for example, 15% sucrose or a mix of sucrose and trehalose) is used in the liquid mixture It was also found that, preferably, the liquid mixture is formulated with a pH of 8.

In addition, low concentrations of NaCl (for example, 0 to 25 mM) are preferably used, and/or low amounts of sorbitol (for example, 0 to 0.75% w/v) sorbitol are preferably added to the mixture Therefore, it was determined that a preferred liquid mixture for colyophylization, where the liquid mixture comprises 3D-MPL, QS21 and the M72 antigen, may be formulated at pH of 8, and that it may comprise: 15% w/v sugar, and 0 to 25 mM NaCl. Preferably, no sorbitol or only low amounts of sorbitol (e.g. between 0 to 0.75% w/v) are added to this mixture.

Example 2—Lyophilised RTS,S/AS01 Vaccine (Quadridose)

RTS,S/AS01 Vaccine
The RTS,S Malaria antigen consists of two polypeptide chains, RTS and S. The RTS polypeptide contains a portion (aa 207-395) of the *P. falciparum* CS protein fused to the surface antigen (S) of the hepatitis B virus. The RTS fusion protein and the S polypeptide are coexpressed in *Saccharomyces cerevisiae* and spontaneously assemble into virus-like particles referred to as RTS,S. These purified particles constitute the RTS,S antigen as used in the formulation of the vaccine. Full details for obtaining the RTS,S antigen are available in WO93/10152, incorporated herein by reference in its entirety. AS01 refers to a vaccine adjuvant comprising QS21, 3D-MPL in a cholesterol containing liposomal formulation.

Concentrated Liposome Bulk
The concentrated liposome bulk was prepared as described in example 3 of WO2013/041572 (incorporated herein by reference in its entirety). Briefly, the concentrated liposome bulk has been prepared in 2 steps. The first step was the lipidic film preparation. DOPC (Dioleoyl phosphatidylcholine), 3D-MPL and cholesterol were dissolved sequentially in isopropanol. Then isopropanol was stripped off under stirring and reduced pressure gradient in a warming bath at 55° C. to obtain a film residue. The pressure was then gradually reduced and a final drying was applied to obtain a lipidic film. The second step was the preparation of the concentrated liposomes bulk. To that end, the lipidic film was rehydrated in PBS to form a coarse suspension of liposomes. The liposome suspension was then homogenized with a high-shear mixer in-line with a high-pressure homogenizer to produce the desired nano-sized liposomes. The resulting concentrated liposome bulk is filtered through a 0.22 μm PES membrane. The concentrated liposome bulk for use in the example contained 40 mg/ml of DOPC, 10 mg/ml Cholesterol, 2 mg/ml MPL in 10 mM phosphate buffer (pH 6.1) and 150 mM NaCl.

Vaccine Formulation
Antigen, i.e. RTS,S, and adjuvant, i.e. AS01, were co-formulated for lyophilisation in water for injection adding
1) 30% sucrose (ad 5%),
2) 100 mM buffer, either PO4 (K/K2) or succinate, pH 6.1 (ad 10 mM),
3) 40 mg/ml liposome bulk (ad 5 mg/ml),
4) 5 mg/ml QS21 (ad 0.25 mg/ml), followed by stirring of the thus obtained adjuvant preparation during 15 to 45 minutes at room temperature. Subsequently 3% (w/v) Polysorbate 80 (ad 0.0312%) was added and the mixture stirred during 15 to 45 minutes at room temperature. The antigen RTS,S was added ad 0.25 mg/ml and the obtained solution stirred for 15-45 minutes at room temperature. pH was measured and adjusted to 6.1 if needed.

Control formulations containing either adjuvant or antigen were also prepared. The samples tested are as follows:
1. RTS,S (lot A) PO4 (Na/Na2) pH 6.8
2. RTS,S (lot B) PO4 (Na/Na2) pH 6.8
3. AS01E3 PO4 (K/K2) pH 6.1
4. colyo RTS,S (lot A)/AS succinate 10 mM pH 6.1
5. colyo RTS,S (lot A)/AS PO4 (K/K2) 10 mM pH 6.1
6. colyo RTS,S (lot B)/AS succinate 10 mM pH 6.1
7. colyo RTS,S (lot B)/AS PO4 (K/K2) 10 mM pH 6.1
8. RTS,S (lot A) succinate pH 6.1
9. RTS,S (lot A) PO4 (K/K2) pH 6.1
10. RTS,S (lot B) succinate pH 6.1
11. RTS,S (lot B) PO4 (K/K2) pH 6.1
12. AS01 succinate pH 6.1
13. AS01 PO4 (K/K2) pH 6.1
14. Sucrose 5%

Freeze-Drying

The formulations thus obtained were filled into glass vials (0.5 ml fill volume) and lyophilized by applying a 28 hour lyophilisation cycle as presented in FIG. 2-A.

Evaluation

Several aspects were assessed to evaluate the thermal stability of the samples for up to 1 year at 4 and 30° C., 6 months at 37° C. and 3 months at 45° C.

1. Visual Aspect of the Cakes

The cakes had an elegant pharmaceutical appearance (similar to MOSQUIRIX® (freeze-dried RTS,S reconstituted with liquid AS01) bidose formulation) for all formulation groups. Intriguingly, the formulations containing RTS,S but not the adjuvant displayed slight retraction. The cake appearance proved to be stable up to 12 months at 30° C. and 6 months at 37° C. A slight shrinkage was observed after 6 months at 45° C., which is probably due to a decrease in Tg because of an increased moist content of the cake.

2. Morphology of the Liposomes by Electron Microscopy

The structure of liposome was also analysed by transmission electron microscopy under a Zeiss Libra120. Negative staining analysis was performed according to standard two-step negative staining method using sodium phosphotungstate as contrasting agent (Hayat M. A. & Miller S. E., 1990, Negative Staining, Mc Graw-Hill ed.), using glow discharged carbon-formvar coated nickel grids (200 mesh) and analyzed at 100 kV. The samples were also analyzed by cryo-microscopy at 80 kV, without any contrasting agent, following vitrification at 107° K in the holes of a carbon-coated plastic mesh (Dubochet et al., 1987, in Cryotechniques in Biological EM; R. A. Steinbrecht and K. Zierold, ed; Springer Verlag). The analysis revealed that in the phosphate-buffered solutions, the liposome morphology was preserved after RTS,S/AS01 co-lyophilization and stable up to 6 months at 45° C.

3. Antigen-Adjuvant Interactions

The interaction between the RTS,S antigen and the AS01 components DOPC and Cholesterol are studied by ultracentrifugation in a sucrose gradient, followed by the quantification of RTS,S, DOPC and cholesterol in the collected fractions. The tested samples were reconstituted in 150 mM NaCl are compared to MOSQUIRIX® (freeze-dried RTS,S reconstituted with liquid AS01). Similar to MOSQUIRIX® (freeze-dried RTS,S reconstituted with liquid AS01), no interaction was observed between RTS,S and the adjuvant components.

4. Liposome Particle Size

Colloidal stability was evaluated by nephelometry, indicating a lightly higher stability of phosphate-buffered formulation compared to succinate-buffered formulations. The size of AS01 liposomes in colyophilized samples was measured by DLS, indicating a hydrodynamic radius of ca 95 nm (the hydrodynamic radius in the control liquid formulation is 110 nm). This is most probably due to the presence of PS80 in the formulation (and not due to the freeze-dying step, neither to the presence of RTS,S). The AS01 liposome size remained stable over time at higher temperature. Results of the nephelometry after incubation at different temperatures are represented in FIG. 4.

5. RTS,S Particle Size

The size of RTS,S particles was measured by SEC-HPLC on a TSKgel G5000PWXL with fluorescence detection (λEx: 280 nm/λEm: 320 nm) in order to avoid interference with adjuvant components when using UV detection. The retention time of RTS,S particles in samples where the adjuvant and antigen were colyophilized was identical to the RTS,S control purified bulk and remained stable up to 1 year at 4 and 30° C., 6 months at 37° C. and 3 months at 45° C.

6. RTS and S Proteins

The integrity of RTS and S proteins was demonstrated by SDS-PAGE and ELISA. SDS-PAGE profiles were similar for up to 1 year at 4 and 30° C., 6 months at 37° C. At 45° C., some slight smears were visible after 3 months of storage. However, antigenicity by ELISA remained stable for up to 1 year at 4 and 30° C., 6 months at 37° C. and 3 months at 45° C. The antigenicity of RTS,S was measured by a mix CS-S sandwich capture ELISA (coating with monoclonal anti-CSP and revelation with a polyclonal anti-S).

7. Chemical Integrity of the Adjuvant Components

The chemical integrity of AS01 components (QS21 and MPL) was evaluated, since both components are known to be sensitive to hydrolysis. Hydrolysed QS21 (QS21H) and MPL congeners are quantified by HPLC methods. QS21 concentration and hydrolysis (QS21H) were determined by reverse phase HPLC on a Symetry RP18 column, with UV detection at 214 nm. MPL congeners were determined following derivatization with DNBA and RP-HPLC on a Waters Symmetry C18 column and fluorescence detection (excitation at 345 nm and emission at 515 nm).

QS21H remained below 3% in all freeze-dried samples. On the contrary, the QS21H content in the liquid reference adjuvant formulation (1 mg/ml DOPC, 0.25 mg/ml Cholesterol, 50 μg/ml QS21, 50 μg/ml MPL in 10 mM phosphatebuffer (pH 6.1), 150 mM NaCl) rapidly increased at high temperature (value above 3% after 1 month at 37° C. and after 3 months at 30° C.).

MPL congeners also remained stable up to 12 months at 30° C. and up to 6 months at 45° C. in all lyophilized formulations. On the contrary, the liquid reference adjuvant formulation is not stable at high temperature, as indicated by MPL deacylation (decrease of the proportion of penta and hexa congeners, together with an increase of the proportion of tetra congeners). The proportion is higher than 35% after 1 month at 45° C., after 3 months at 37° C. or after 6 months at 30° C.

8. Preclinical Immunogenicity

Immunogenicity of the co-lyophilized samples was compared to the immunogenicity of Mosquirix™ in a mouse model. The antibody responses and CD8 T-cell responses against both S and CS antigen were evaluated, as well as CD4 responses against S antigen were assessed in CB6F1 mice.

Fresh pools of leukocytes collected at different time points, were stimulated for 6 hours with pools of 15-mer peptides covering the CSP or HBs sequence. The CSP and HBs-specific cellular responses were evaluated by ICS measuring the amount of CD4+ or CD8+ T cells expressing IFN-γ and/or IL-2 and/or TNFα. All ICS analysis were performed using FlowJo software.

The study results showed that the co-lyophilization of RTS,S and AS01 had no impact on the immunogenicity (same cellular and humoral responses for both RTS and S at T0, compared to the current MOSQUIRIX® (freeze-dried RTS,S reconstituted with liquid AS01).

Also, the co-lyophilization RTS,S/AS01 proved to be stable up to 1 year at 30° C. (and 1 year at 30° C. plus 1 month at 45° C.), 6 months at 37° C. and 3 months at 45° C. (except a slight increase of HBs-specific CD8+ T cell responses observed after 3 months at 37° C. but not at 45° C.). Upon reconstitution of lyophilized RTS,S in the liquid reference adjuvant formulation pre-incubated for 3 months at 37° C., there was a slight decrease of CSP-specific CD4+ T cell responses). The liquid reference adjuvant formulation incubated for 3 months at 45° C. could not be injected because it was proven to be haemolytic. Immune response is illustrated by FIG. 3.

Example 3—Lyophilised VZV gE/AS01 Vaccine (Unidose)

The VZV gE antigen (also referred to herein as gE) is a truncated form of the Varicella Zoster Virus glycoprotein E, has the sequence as disclosed in FIG. 5, and is obtained as disclosed in Example 2 of WO2006/094756. AS01 refers to the vaccine adjuvant comprising QS21, 3D-MPL in a cholesterol containing liposomal formulation.

The concentrated liposome bulk used is the same as described for Example 2.

The antigen, i.e. VZV gE, and adjuvant, i.e. AS01, were co-formulated for lyophilisation in water for injection mixing:
1) 30% sucrose (ad 5%),
2) 100 mM buffer, either PO4 (K/K2), pH 6.1 (ad 10 mM),
3) 40 mg/ml liposome bulk (ad 2.5 mg/ml), and,
4) 5 mg/ml QS21 (ad 0.125 mg/ml), followed by stirring of the thus obtained adjuvant preparation during 15 to 45 minutes at room temperature. Subsequently 3% (w/v) Polysorbate 80 (ad 0.02%) was added and the mixture stirred during 15 to 45 minutes at room temperature. The antigen VZV gE was added ad 0.125 mg/ml and the obtained solution was stirred for 15-45 minutes at room temperature. pH was measured and adjusted to 6.1 if needed.

Control formulations containing either adjuvant or antigen were also prepared. The samples tested were as follows:
1) VZV gE/AS01
2) VZV gE
3) AS01

Freeze-Drying

The formulations thus obtained were filled into glass vials (0.5 ml fill volume) and lyophilized by applying a 40-hour lyophilisation cycle as represented in FIG. 2-B.

Evaluation

The purpose of this experiment was to evaluate the feasibility of co-lyophilisation of another antigen (VZV gE) with the adjuvant AS01. The integrity of both antigen and adjuvant were evaluated directly after co-lyophilisation.

The lyophilised material was analysed following reconstitution with 150 mM NaCl and compared to control VZV gE vaccine (lyophilized VZV gE reconstituted in liquid AS01 or in buffered saline (10 mM phosphate, 150 mM NaCl, pH 6.1).

1. Injectability

The pH measured in the different groups are slightly lower (by ca. 0.4 units) that in the control Shingrix vaccine, although the pH was fixed at 6.1 in the corresponding final bulks (before lyophilisation). The osmolality determined in the 3 groups is similar to the control.

| Group | | PH | Osmolality (mOsm/kg) |
|---|---|---|---|
| 1 (colyo gE/AS) | Before lyophilisation | 6.1 | 206 |
| | After lyophilisation | 5.8 | 436 |
| 2 (gE) | Before lyophilisation | 6.1 | 208 |
| | After lyophilisation | 5.8 | 432 |
| 3 (AS01) | Before lyophilisation | 6.1 | 209 |
| | After lyophilisation | 5.8 | 430 |
| Control | | 6.2 | 436 |

2. Morphology of the Liposomes by Electron Microscopy

The structure of liposomes was also analysed by transmission electron microscopy with negative staining, using the same protocol as in Example 2.

The adjuvant displayed the characteristic morphology of the AS01 structural pattern at the EM level, i.e. liposomes of various size and shape, with membrane perforations clearly visible. The putative gE antigens were observed as very small amorphous material spread between liposomes.

The same pattern was observed in the gE/AS01 sample before and after lyophilisation, and in the to control gE cake reconstituted in AS01 adjuvant, indicating that the liposome morphology was preserved after gE/AS01 co-lyophilization.

3. Liposome Particle Size

The size of AS01 liposomes in samples was measured by DLS (in the groups containing AS01), indicating a hydrodynamic radius of ca 90 nm similar to the hydrodynamic radius in the control liquid formulation. The value obtained was close to the expected value for AS01 liposome.

| Group | | DLS_ZAD (nm) |
|---|---|---|
| VZV gE/AS01 | Before lyophilisation | 93 |
| | After lyophilisation | 91 |
| AS01 | Before lyophilisation | 91 |
| | After lyophilisation | 91 |

4. Size of gE in Solution

The size of gE antigen was measured by SEC-HPLC on a TSKgel G4000PWXL with fluorescence detection (λEx: 280 nm/λEm: 320 nm) in order to avoid interference with adjuvant components when using UV detection. The retention time of VZV gE in samples where the adjuvant and antigen were colyophilized was identical to the gE control purified bulk, indicating that the colyophilization process had no impact on the size of gE in solution.

5. Integrity of gE Protein

The integrity of VZV gE protein was demonstrated by SDS-PAGE analysis of samples before and after lyophilisation. SDS-PAGE profiles (see FIG. 6) were similar for co-lyophilized samples and VZV gE control (purified bulk and drug product), in both reducing (R) and non-reducing (NR) conditions. A slight band of higher molecular weight was observed in co-lyophilized sample, corresponding presumably to aggregation, but not representing a significant amount of protein.

Figure 6:
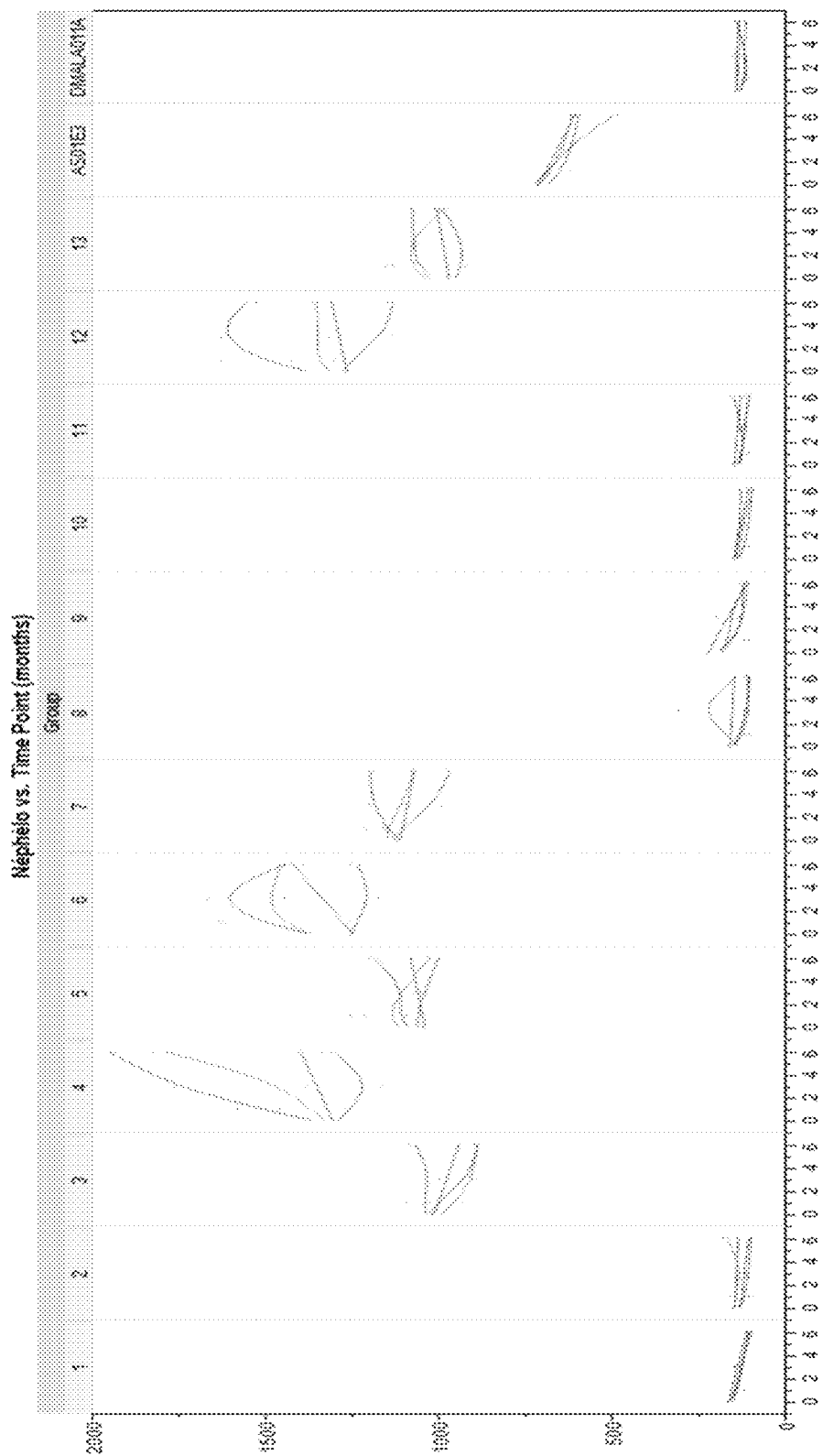
FIG. 6 illustrates the nephelometry data as obtained in Example 2.
Figure 9:
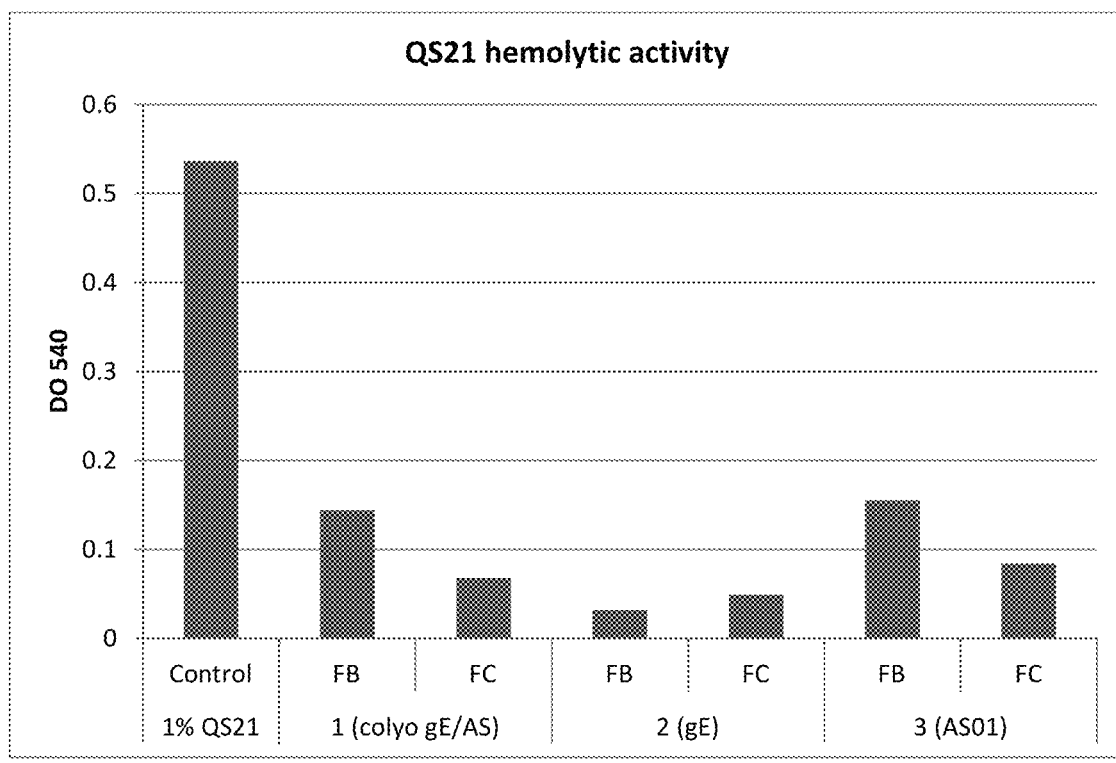
FIG. 9 shows the results of the analysis of the impact of lyophilisation on QS21 haemolytic activity in Example 3; FB refers to the composition before lyophilisation, FC refers to the composition after lyophilisation.

Legend for FIG. 6

| | |
|---|---|
| 1 | MW marker |
| 2 | Sample buffer |
| 3 | Control VZV gE (purified bulk) |
| 4 | Control VZV gE (reconstituted in AS01 buffer) |
| 5 | Sample buffer |
| 6 | VZV gE/AS01 before colyo (group 1) |
| 7 | VZV gE before lyo (group 2) |
| 8 | AS01 before lyo (group 3) |
| 9 | Colyo VZV gE/AS01 (group 1) |
| 10 | Lyo VZV gE (group 2) |
| 11 | Lyo AS01 (group 3) |
| 12 | Sample buffer |

6. In Vitro Potency (Antigenic Activity by ELISA)

The in vitro potency was measured by ELISA in the samples containing VZV gE. The test is an inhibition ELISA assay based on a human polyclonal antibodies directed against Varicella Zoster antigens (VARITECT®).

Briefly, serial dilutions of samples containing VZV gE antigen are incubated with a fixed amount of VARITECT®. After incubation, human anti-gE antibodies, which do not react with VZV gE antigen samples are detected by incubation on gE antigen coated microplate. The antigen-antibody complex is revealed by addition of a rabbit anti-human IgG antibody labelled with peroxidase, followed by addition of tetra methyl benzidine. The VZV gE antigenic activity is obtained by dividing the VZV gE content by the protein content (measured by Lowry). The potency, which can only be applied to final containers, is obtained by dividing the VZV gE content by the titer of the standard that was used for the validation of the method.

The ratio of in vivo potency to VZV gE content was close to 1 in all tested groups, as in the control. These results further confirmed the integrity of VZV gE antigen following lyophilisation in the presence of AS01.

| | Theoretical gE content (µg/ml) | Protein content by Lowry (µg/ml) | gE content by ELISA (µg/ml) | Antigenic activity (gE/prot) | Potency |
|---|---|---|---|---|---|
| gE/AS01 no lyo (group 1) | 125 | 128 | 123 | 0.96 | N/A |
| Colyo gE/AS01 (group 1) | 100 | 104 | 103 | 0.99 | 1.02 |
| gE no lyo (group 2) | 125 | 125 | 132 | 1.05 | N/A |
| Lyo gE (group 2) | 100 | 100 | 101 | 1.01 | 0.98 |
| Control | 100 | 94 | 108 | 1.15 | 0.92 |

7. Chemical Integrity of the Adjuvant Components

As in Example 2, the chemical integrity of AS01 components (QS21 and MPL) was evaluated in AS01-containing samples. Hydrolysed QS21 (QS21H) and MPL congeners were quantified by HPLC methods. QS21H remained below 3% in all freeze-dried samples. There was no impact of the lyophilisation process on the chemical integrity of MPL, as indicated by the similar proportions of tetra-, penta- and hexa-congeners before and after lyophilisation in both groups.

| Test | Acceptance criteria for AS01B3 | Group 1 (gE/AS01) liquid | Group 1 (gE/AS01) Colyo | Group 3 (AS01) liquid | Group 3 (AS01) Lyo |
|---|---|---|---|---|---|
| QS21H LIMIT TEST BY HPLC | Not more than 3%. | <3% | <3% | <3% | <3% |
| MPL CONGENER DISTRIBUTION BY HPLC-FLUO (Tetra-acyl component) | Between 15 and 35%. | 23.9 | 24.7 | 24.5 | 24.3 |
| MPL CONGENER DISTRIBUTION BY HPLC-FLUO (Penta-acyl component) | Between 35 and 60%. | 44.8 | 44.2 | 44.8 | 45 |
| MPL CONGENER DISTRIBUTION BY HPLC-FLUO (Hexa-acyl component) | Between 20 and 40%. | 31.3 | 31.1 | 30.7 | 30.7 |

QS21 elicits a haemolytic activity when not quenched with cholesterol within the liposomal membrane. The hemolytic activity was therefore evaluated in the AS01 containing formulations, before and after lyophilisation. Whatever the conditions tested, the hemolytic rate remained under the acceptable baseline fixed at 1% (see FIG. 7). None of them were responsible for a QS21 dequenching.

The invention claimed is:

1. A composition dried under reduced pressure by lyophilisation from a liquid mixture comprising:
   (a) an adjuvant which comprises 3-deacylated monophoshoryl lipid A (3D-MPL) and QS21 in a liposomal formulation, wherein the liposomes contain dioleoyl phosphatidylcholine (DOPC) and cholesterol,
   (b) amorphous sugar, wherein the amorphous sugar is present in an amount of more than 7.5% (w/v) of the liquid mixture, and
   (c) an antigen derived from *Mycobacterium tuberculosis*, wherein the antigen comprises a sequence having at least 90% identity to SEQ ID No: 3, and wherein the adjuvant and the antigen are co-vialed during the lyophilisation.

2. A composition according to claim 1, wherein the antigen comprises a sequence having at least 95% identity to SEQ ID No:3.

3. A composition according to claim 2, wherein the antigen comprises the amino acid sequence of SEQ ID No:4.

4. A composition according to claim 1, wherein the liquid mixture comprises at least 10% (w/v) amorphous sugar.

5. The composition according to claim 4, wherein the concentration of sodium chloride in the liquid mixture is below 50 mM, and the concentration of sorbitol in the liquid mixture is less than 1.0% (w/v).

6. The composition according to claim 4, wherein the concentration of sodium chloride in the liquid mixture is from 0 to 25 mM, and the concentration of sorbitol in the liquid mixture is from 0 to 0.75% (w/v).

7. The composition according to claim 6, wherein the ratio of amorphous sugar to sorbitol in (w/v) % is between 5:1 and 20:1.

8. A composition according to claim 1, wherein the amorphous sugar is a combination of sucrose and trehalose.

9. A composition according to claim 1, wherein the concentration of sodium chloride in the liquid mixture is below 50 mM.

10. A composition according to claim 1, wherein the conductivity of the liquid mixture is 13 mS/cm or lower.

11. A composition according to claim 1, wherein the concentration of salts in the liquid mixture is 130 mM or lower.

12. A composition according to claim 1 wherein the liquid mixture further comprises sorbitol.

13. A composition according to claim 12 wherein the concentration of sorbitol in the liquid mixture is less than 6% (w/v %).

14. A composition according to claim 13 wherein the concentration of sorbitol in the liquid mixture is less than 2% (w/v).

15. A composition according to claim 1 wherein the liquid mixture has a pH between 6 and 9.

16. A composition according to claim 1 wherein the liquid mixture further comprises a buffer.

17. A composition according to claim 1 wherein the liquid mixture further comprises a surfactant.

18. A vaccine comprising the composition of claim 1.

19. The composition according to claim 1, wherein the concentration of sodium chloride in the liquid mixture is below 50 mM, and the concentration of sorbitol in the liquid mixture is less than 1.0% (w/v).

20. The composition according to claim 1, wherein the concentration of sodium chloride in the liquid mixture is from 0 to 25 mM, and the concentration of sorbitol in the liquid mixture is from 0 to 0.75% (w/v).

21. The composition according to claim 20, wherein the ratio of amorphous sugar to sorbitol in (w/v) % is between 5:1 and 20:1.

22. A liquid mixture comprising:
a. an adjuvant which comprises 3-deacylated monophoshoryl lipid A (3D-MPL) and QS21 in a liposomal formulation, wherein the liposomes contain dioleoyl phosphatidylcholine (DOPC) and cholesterol,
b. amorphous sugar, wherein the amorphous sugar is present in an amount of more than 7.5% (w/v) of the liquid mixture, and
c. an antigen derived from *Mycobacterium tuberculosis*, wherein the antigen comprises a sequence having at least 90% identity to SEQ ID No: 3.

23. A vaccine comprising the liquid mixture of claim 22.

24. A method for producing the dried composition of claim 1, wherein the method comprises the steps of:
(i) Preparing a liquid mixture comprising:
(a) QS21,
(b) liposomes containing dioleoyl phosphatidylcholine (DOPC) and cholesterol,
(c) amorphous sugar, wherein the amorphous sugar is present in an amount of more than 7.5% (w/v) of the liquid mixture,
(d) an antigen derived from *Mycobacterium tuberculosis*, wherein the antigen comprises a sequence having at least 90% identity to SEQ ID No: 3, and
(e) 3-deacylated monophoshoryl lipid A (3D-MPL); and
(ii) drying the mixture under reduced pressure, wherein (a)-(e) are co-vialed during the drying.

25. A method of vaccination comprising:
(a) taking a composition according to claim 1;
(b) reconstituting the composition with an isotonic solution; and
(c) administering the reconstituted composition to a mammal;
wherein the composition comprises 10 to 75 μg of 3-deacylated monophoshoryl lipid A (3D-MPL), 10 to 75 μg of QS21 and 1 to 50 μg of an antigen derived from *Mycobacterium tuberculosis*, and wherein the antigen comprises a sequence having at least 90% identity to SEQ ID No: 3.

* * * * *